US012758247B2

(12) United States Patent
Podmore et al.

(10) Patent No.: US 12,758,247 B2
(45) Date of Patent: Oct. 13, 2026

(54) SYSTEMS FOR TREATING TISSUE

(71) Applicant: REVELLE AESTHETICS, INC., Mountain View, CA (US)

(72) Inventors: Jonathan Podmore, San Carlos, CA (US); Earl Bright, II, Sunnyvale, CA (US); Joshua Makower, Los Altos Hills, CA (US); Arthur Ferdinand, Gilroy, CA (US); Amanda White, Mountain View, CA (US); Pablo Acosta, Newark, CA (US); John Hanley, Manhattan Beach, CA (US)

(73) Assignee: Revelle Aesthetics, Inc., Mountain View, CA (US)

( * ) Notice: Subject to any disclaimer, the term of this patent is extended or adjusted under 35 U.S.C. 154(b) by 1122 days.

(21) Appl. No.: 17/866,744

(22) Filed: Jul. 18, 2022

(65) Prior Publication Data

US 2022/0347496 A1 Nov. 3, 2022

Related U.S. Application Data

(63) Continuation of application No. PCT/US2021/013887, filed on Jan. 19, 2021.
(Continued)

(51) Int. Cl.
*A61B 17/32* (2006.01)
*A61H 9/00* (2006.01)
(Continued)

(52) U.S. Cl.
CPC .................. *A61B 17/32002* (2013.01); *A61B 17/320068* (2013.01); *A61H 9/0057* (2013.01);
(Continued)

(58) Field of Classification Search
CPC .............. A61Q 19/06; A61B 17/32002; A61B 17/320068; A61B 2017/00017; A61B 2017/00115; A61B 2017/00128; A61B 2017/00907; A61B 2017/00946; A61B 2090/064; A61B 2090/08021; A61B 17/3421; A61B 17/3478; A61B 2017/00323; A61B 2017/308; A61B 17/320016; A61B 2017/00761; A61B 2017/320028; A61B 17/32093; A61B 2017/320056; A61B 2017/32006;
(Continued)

(56) References Cited

U.S. PATENT DOCUMENTS 5,478,347 A 12/1995 Aranyi
5,649,947 A 7/1997 Auerbach et al.
(Continued)

FOREIGN PATENT DOCUMENTS

CN 201617909 11/2010
CN 202154724 3/2012
(Continued)

*Primary Examiner* — Theodore J Stigell
(74) *Attorney, Agent, or Firm* — Blank Rome LLP

(57) ABSTRACT

Systems and methods for treating cellulite including an apparatus that applies or a method involving separating septa to eliminate or reduce the appearance of cellulite. In one approach, an interventional tool is placed between tissue layers to engage and treat septa connecting tissue layers between which fat deposits are contained.

15 Claims, 19 Drawing Sheets

Related U.S. Application Data

(60) Provisional application No. 62/964,566, filed on Jan. 22, 2020, provisional application No. 62/963,602, filed on Jan. 21, 2020.

(51) Int. Cl.
*A61N 5/06* (2006.01)
*A61Q 19/06* (2006.01)

(52) U.S. Cl.
CPC ...... *A61Q 19/06* (2013.01); *A61H 2201/0153* (2013.01); *A61N 2005/065* (2013.01)

(58) Field of Classification Search
CPC .... A61B 2017/3409; A61B 2017/3445; A61B 2090/061; A61B 2090/062; A61B 2090/306; A61B 2090/3945; A61H 9/0057; A61H 2201/0153; A61N 2005/065
See application file for complete search history.

(56) References Cited

U.S. PATENT DOCUMENTS

| | | | | |
|---|---|---|---|---|
| 5,728,112 | A | 3/1998 | Yoon | |
| 5,749,147 | A | 5/1998 | Hasegawa | |
| 6,377,854 | B1 | 4/2002 | Knowlton | |
| 7,217,265 | B2 | 5/2007 | Hennings et al. | |
| 7,442,192 | B2 | 10/2008 | Knowlton | |
| 7,671,423 | B2 | 3/2010 | Voldman | |
| 7,771,374 | B2 | 8/2010 | Slatine | |
| 7,871,423 | B2 | 1/2011 | Livneh | |
| 8,167,280 | B2 | 5/2012 | Chomas et al. | |
| 8,348,867 | B2 | 1/2013 | Deem et al. | |
| 8,439,940 | B2 | 5/2013 | Chomas et al. | |
| 8,652,123 | B2 | 2/2014 | Gurtner | |
| 8,979,881 | B2 | 3/2015 | Clark, III | |
| 9,358,033 | B2 | 6/2016 | Ballakur et al. | |
| 9,539,439 | B2 | 1/2017 | Jones et al. | |
| 9,550,052 | B2 | 1/2017 | Ignon et al. | |
| 9,615,882 | B2 | 4/2017 | Shroff et al. | |
| 9,919,168 | B2 | 3/2018 | Altshuler et al. | |
| 9,974,519 | B1 | 5/2018 | Schwarz et al. | |
| 10,117,892 | B2 | 11/2018 | Perry | |
| 10,271,866 | B2 | 4/2019 | Clark, III | |
| 10,888,348 | B2 | 1/2021 | Gutwein et al. | |
| 11,013,527 | B1 | 5/2021 | Podmore et al. | |
| 11,116,888 | B2 | 9/2021 | Bright, II et al. | |
| 2003/0130628 | A1 | 7/2003 | Duffy | |
| 2003/0158566 | A1 | 8/2003 | Brett | |
| 2004/0204734 | A1 | 10/2004 | Wagner et al. | |
| 2004/0243159 | A1 | 12/2004 | Shiuey | |
| 2004/0260210 | A1 | 12/2004 | Ella et al. | |
| 2005/0251120 | A1 | 11/2005 | Anderson et al. | |
| 2006/0172255 | A1 | 8/2006 | Hochman et al. | |
| 2006/0241663 | A1 | 10/2006 | Rice et al. | |
| 2006/0241673 | A1 | 10/2006 | Zadini et al. | |
| 2008/0015624 | A1 * | 1/2008 | Sonoda ................. | A61M 5/425 606/185 |
| 2008/0058603 | A1 | 3/2008 | Edelstein et al. | |
| 2008/0109023 | A1 | 5/2008 | Greer | |
| 2008/0200863 | A1 | 8/2008 | Chomas et al. | |
| 2009/0093737 | A1 | 4/2009 | Chomas et al. | |
| 2009/0248004 | A1 | 10/2009 | Altshuler et al. | |
| 2009/0275899 | A1 | 11/2009 | Deem et al. | |
| 2010/0004581 | A1 * | 1/2010 | Brigatti ................ | A61N 5/1017 604/20 |
| 2010/0106063 | A1 | 4/2010 | Chomas et al. | |
| 2010/0237163 | A1 | 9/2010 | Chomas et al. | |
| 2010/0256596 | A1 | 10/2010 | Chomas | |
| 2011/0028898 | A1 * | 2/2011 | Clark, III ........... | A61B 18/1477 604/93.01 |
| 2011/0295297 | A1 | 12/2011 | Shirley et al. | |
| 2011/0319839 | A1 | 12/2011 | Del Vecchio | |
| 2012/0022510 | A1 | 1/2012 | Welches et al. | |
| 2012/0150208 | A1 | 6/2012 | Messmer | |
| 2013/0123771 | A1 | 5/2013 | Clark, III et al. | |
| 2013/0190739 | A1 | 7/2013 | Clark, III et al. | |
| 2013/0190740 | A1 | 7/2013 | Clark, III et al. | |
| 2013/0197427 | A1 | 8/2013 | Merchant et al. | |
| 2014/0276693 | A1 | 9/2014 | Altshuler et al. | |
| 2015/0064165 | A1 * | 3/2015 | Perry ................. | A61B 17/3421 424/94.67 |
| 2018/0116905 | A1 | 5/2018 | Capelli et al. | |
| 2018/0214169 | A1 | 8/2018 | Gutwein et al. | |
| 2019/0046738 | A1 | 2/2019 | Banker | |
| 2020/0046391 | A1 | 2/2020 | Capelli et al. | |
| 2021/0093898 | A1 | 4/2021 | Pooth et al. | |

FOREIGN PATENT DOCUMENTS

| | | | |
|---|---|---|---|
| CN | 202821527 | | 3/2013 |
| CN | 204191319 | | 3/2015 |
| CN | 104644244 | | 5/2015 |
| CN | 204500879 | | 7/2015 |
| EP | 2504047 | | 10/2012 |
| GB | 2350080 | A | 11/2000 |
| WO | WO2019060924 | | 3/2019 |

* cited by examiner

SYSTEMS FOR TREATING TISSUE

FIELD OF THE DISCLOSURE

The present disclosure generally relates to systems and methods for treating cellulite.

BACKGROUND OF THE DISCLOSURE

There is a continuing need for an effective approach to treating cellulite, also known as gynoid lipodystrophy, nodular liposclerosis, edematofibrosclerotic panniculopathy, panniculosis, adiposis edematosa, demopanniculosis deformans or status protrusus cutis. Moreover, there is a need for proactive treatment modalities that prevent future or reoccurrence of cellulite and which are easy and effective to use.

It has been reported that more than 85% of women have cellulite thus suggesting that cellulite is a physiologic rather than pathologic condition. The existence of fat in the reticular dermis alone is not thought to cause cellulite. Cellulite can be described as the herniation of subcutaneous fat within fibrous connective tissue that is expressed as dimpling of the skin. This fat loading can lead to stress on connective tissue located between fat lobulas. Such dimpling is more common in women than men due to the orientation of subcutaneous fibrous structures defining chambers containing fat cells. In fact, it is this structure that is believed to cause the appearance of cellulite more than being overweight. Often, cellulite appears on the pelvic region including the buttocks, lower limbs and abdomen.

Subdermal fat layers below the epidermis are contained between dermal layers connected by septa which act as connective tissue between the dermal layers. In men, the septa are arranged more randomly and densely oriented in a more criss-crossed configuration while the septa in women are generally more parallel in arrangement. Also, men have thicker dermis and more angled septa relative to the skin surface whereas women have relatively thinner dermis which thins with age, and septa that are perpendicular to the skin surface. Moreover, women with cellulite have exhibited thickening of the septa in the regions of cellulite and tensioning of septa highlights cellulite. In women, fat storage in adipose tissue has a biological purpose in that it is maximized ensuring adequate caloric availability for pregnancy and lactation. An increase in fluid retention or proliferation of adipose tissue in such subdermal fat layers can further result in the appearance of cellulite where the septa is maintaining a first distance between dermal layers, thus creating dimples, whereas pockets between septa bulge. Over time, the septa may stretch, then eventually contract and harden thus retaining tissue layers at fixed distances, but pockets between such septa may be expanded thus adding to the appearance of cellulite.

Various approaches have been taken to treat or address cellulite. Early treatments involved attempts at increasing circulation and fat oxidation in areas exhibiting cellulite. Here, substances such as hyaluronic acid and aminophylline were injected in the target areas to reduce cellulite. Other approaches involved electroporating the target areas followed by the application of mesotherapy, or applying dermological creams or other supplements to cellulite. These approaches could be supplemented by massage or massage was used alone for the purpose of promoting increased fat reabsorption or drainage of fluids and toxins in the treated areas. Ultrasound has also been proposed to disrupt subcutaneous tissues and fat and has been used in combination with liposuction. Low acoustic pressure in combination with the infiltration of microbubbles has also been employed to reduce the appearance of cellulite, as has the use of other energies such as lasers and radio frequency. Such approaches have been characterized by limited or unpredictable results. More recently, the cutting of septa with blades or needles in the subdermal region has been employed. Prior approaches have been found to be labor intensive and very traumatic to the tissue leading to bleeding, bruising, tough tissue nodules, long, painful recoveries and inconsistent results.

Yet further approaches involved a minimally invasive subcutaneous treatment device involving a handpiece having a recessed area for receiving tissue, a treatment tool insertable into the recessed area, and a guidance track operably connected to the handpiece, wherein the guidance track is configured to constrain a portion of the tool in contact with the guidance track to move along a predetermined path to cooperatively move a distal end of the tool within the recessed area defined by the predefined path. However, various limitations are associated with this approach including a lack of automation, ability to isolate or verify disruption of target tissue, device tracking and visualization, and customization.

Accordingly, there is a need for additional strategies to effective and efficient approaches to treating, minimizing or eliminating cellulite with simple systems that minimize trauma. These approaches should be associated with predictable results and be relatively easy to employ.

The present disclosure addresses these and other needs.

SUMMARY OF THE DISCLOSURE

Briefly and in general terms, the present disclosure is directed towards cellulite treatment systems and methods involving an apparatus that facilitates and methods involving stretching, re-orienting, disrupting, cutting, slicing, and/or tearing septum or septa in a location of cellulite. In one aspect, the treatment approach involves a tissue cutting or slicing system.

In one or more embodiments, devices and methods are provided to minimally invasively create a limited planar dissection at a defined depth below the dermis through septa. In particular, the plane of dissection may be created generally parallel to and at a predefined depth below the dermis. Alternatively, a limited plane of dissection may be created at an angle or in a curved shape relative to the surface of the dermis. Additionally, the devices and methods are used to create a small tissue pocket created by the dissection by applying a vacuum assisted suction force to a handpiece during the performance of the dissection and lifting the skin after the dissection is completed. The small pocket can be filled with the patient's adipose tissue harvested from other locations or with other fillers or spacers. Alternatively, adhesive is used to accomplish lifting. Application of such forces on the skin during the dissection process puts traction on the underlying tissues, may better align the fibrous septa for dissection with the cutting tool, and allows for uniform and instantaneous separation of the dissected tissue layers. Additionally, devices and methods are disclosed for applying lifting forces to a skin area overlying treated subcutaneous tissue after creation of the dissection. A range of approaches are provided that are capable of creating dissections and/or achieving coagulation and hemostasis or a combination of these treatment modalities, thereby enabling tailoring the treatment to the individual patient.

In one or more of the disclosed approaches, structure is provided to selectively protect tissue from cutting structure so as to improve incision site healing. Moreover, in one or more embodiments, methods are provided to reduce bruising from suction or other tissue lifting approaches such as providing custom shaped handpieces and decreasing or monitoring tissued lifting structures. Additionally, there are provided structure and approaches that reduce pain and recovery by treating more localized and focused areas, being able to verify that target septa is treated and by decreasing variability of results and operator intervention times through automation.

In one embodiment, a cellulite treatment device is mounted at a distal end portion of a shaft and is sized and shaped to be advanced between tissue layers. In one particular aspect, fibrous septa that connect superior and inferior fascia plateaus within skin can be crossed with the treatment device using one or more of an array of tools to engage, and depending on the tool used and force applied by the user, stretch, re-orient, tear, disrupt, cut or slice septa. By doing so, the target subcutaneous connective tissue associated with the surface defect can be directly modified with minimal impact to surrounding blood vessels and lymphatic system and fat can be more evenly distributed and skin can assume a smoother appearance.

In one or more aspects, a cellulite treatment system embodies a tool facilitating an ability to reach and treat all target cellulite appearance areas through a single or a limited number of entries through the skin. In certain aspects, such tool is sized, shaped and configured (e.g. less than or equal to about two-three millimeters diameter and having a blunt dissection tip) to be placed within and advanced between tissue layers. Entry points through the skin such as high on the hip under where a bikini or underwear strap would be and along creases or transitions between buttocks and thighs are employed. Identification and assessment of target septa is accomplished by pushing, pulling or otherwise tensioning septa in areas believed to be associated with the expression of cellulite on the outside of skin. It has been recognized that septa causing a dimple or depression are located at various angles and locations relative to the dimple or depression observed on the skin and are not necessarily directly below such expressions of cellulite, and the treatment system and method is configured to identify the septa responsible for the appearance of cellulite and target treatment on those septa and leave adjacent septa, blood vessels, etc. intact. Moreover, a range such as a small subset or a larger number of septa can be the structure causing a particular depression or dimple.

In one method, anesthetic is injected into the treatment site transcutaneously or subcutaneously, a cellulite treatment system is inserted subcutaneously across the treatment site and used to identify the septa responsible for a depression or dimple by pushing or pulling on various septa to cause a depression in the skin in the target area, and a cutting or slicing device or septa disruption structure is placed subcutaneously at the treatment site and employed to engage and cut or slice or break the septa tissue. Remote imaging or ultrasonic or fluoroscopic energy can be employed to observe the procedure. A resizing or alternative configuration of the treatment structure can be employed to complete the treatment of a particular area. The treatment device is then repositioned to treat additional areas. The treatment device can be configured to treat a plurality of areas simultaneously or in succession without removing from the patient or a spot treatment approach can be taken. Additionally, through one or more entry points, various treatment trajectories are directed and in certain applications a steerable introducer is used to access treatment areas. Further, anti-inflammatory, collagenase, deoxycholic acid, salicylic acid, glycolic acid, hyaluronic acid or cellulite treatment medicants can be employed at the interventional site separately or directly by the interventional device or other procedural instrumentation. Aspects of the current approach include specific identification of the septa responsible for the cellulite appearance, severing or separation of those septa, confirmation intra-operatively of the separation of those septa was accomplished and the prevention of the re-appearance of the cellulite.

In one approach, the treatment device comprises a handpiece including structure defining a recessed area, one or more conduits extending through a side of the recessed area, a tool configured to at least partially extend through the one or more conduits and into the recessed area and a guidance track operably connected to the handpiece, wherein the guidance track is configured to constrain a portion of the tool in contact with the guidance track to move along a predetermined path to cooperatively move a distal end of the tool within the recessed area in a plane substantially parallel to a top of the handpiece and within a region of a predetermined shape defined by the predefined path.

In one aspect, the handpiece conforms to a patient's anatomy. In an additional or alternative embodiment, the path taken by the treatment device within tissue is guided by a controller in communication with a tool control mechanism and is programmable for a specific patient's treatment regimen. Transillumination is employed to provide the operator with information regarding the positioning of the treatment device within tissue. The device further comprises an entry disposed on an inner side of the conduit and facing the recessed area, the entry hole defining a tool pivot point when a distal end of the tool is inserted through the conduit and into the recessed area. In some aspects, the device may also comprise a platform operatively connected to the handpiece, wherein the platform includes the guidance track, and a guide pin operably connected to the tool, said guide pin slidably engaging the guidance track such that the tool is constrained to move in accordance with the predetermined path. The tool further comprises a cutting blade and in one specific aspect, a reciprocating motor coupled to the cutting blade, the reciprocating motor reciprocating the cutting blade. The tool may further include a sleeve, wherein the cutting blade is at least partially slidably disposed within the sleeve. Also, a vacuum conduit extending through a side of the perimeter elevation to the recessed area. In some aspects the vacuum conduit can be connected to a vacuum device. The handpiece is configured to be adjustable and configured to change the distance between an inner side of the top of the handpiece and changes a volume of the recessed area when the top is adjusted.

Methods for performing subcutaneous surgery in a region underlying skin tissue having a deformity, involve or include positioning a handpiece having a recessed area over a section of skin, reducing air pressure or otherwise volume inside the recessed area to move a portion of the section of skin and a subcutaneous tissue into the recessed area, inserting a dissection tool through a conduit in the handpiece and through the section of skin into the subcutaneous tissue, and creating a dissection in the subcutaneous tissue, wherein the deformity is selected from for example, a scar, a wrinkle, and a surface irregularity resulting from liposuction, and following creation of the dissection an appearance of the deformity is improved.

In various aspects, the treatment device can include one or more of projecting linkages or energy transmitting structure for disrupting, cutting, slicing or dissecting tissue and/or controlling bleeding. In one particular approach, the treatment device includes a mechanical septa cutting element, such as a blade or sharpened surface, that cooperates with a septa hooking element to both hook then cut, slice, tear or disrupt septa. One or more of the septa hooking element and the septa cutting element is convertible from a hooking configuration to a cutting configuration and from a cutting configuration to a hooking configuration or to a stored configuration. In another particular approach, the treatment device is embodied in an elongate member insertable through the skin capable of expanding at least one region from a smaller state to a wider state, and when in the wider state is configurable to both hook and cut, slice or disrupt target septa. In one or more alternative or additional aspects, cutting or disruption is accomplished with electrical or thermal means such as mono-polar or bi-polar structures or a hot wire configured to address bleeding and ease cutting.

The cellulite treatment system also involves in certain approaches, illumination such as a bright light configured at or emitted through a tip of treatment structure or placed along or at strategic locations along treatment structure for the purposes of tracking advancement of the tool to the treatment site and locating intra-dermal structures at the treatment site. In this way, direct observation of the treatment device by transillumination through the skin is provided and positioning and performance thereof subcutaneously is readily available to an operator.

Additionally, the disclosed devices and structures are employed for body sculpting, eliminating wrinkles, treating acne scars and/or repositioning skin. Foam fillers or spacers of varying lengths and other structures such as adipose tissue or subcutaneous attachment structures that are absorbable or permanent are used to accomplish such objectives.

These and other features of the disclosure will become apparent to those persons skilled in the art upon reading the details of the systems and methods as more fully described below.

DETAILED DESCRIPTION OF THE DISCLOSURE

Figure 1A:
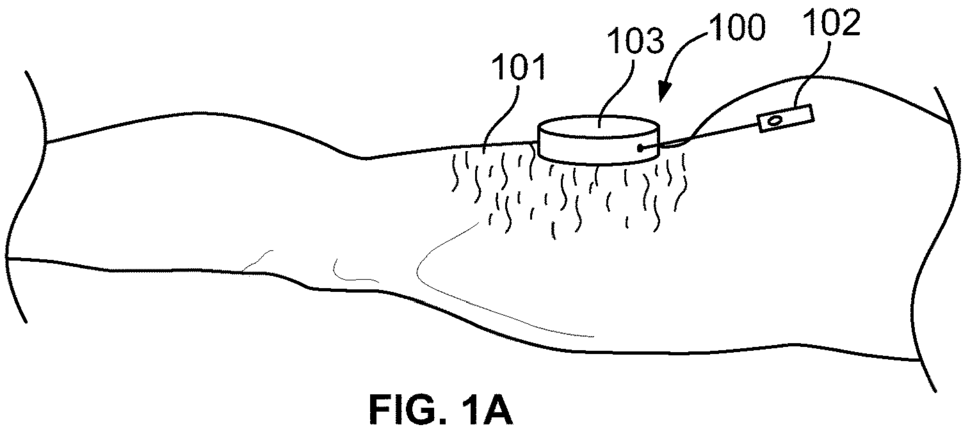
FIGS. 1A-B depict a dissection device, including a handpiece and a cutting tool.

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described.

It must be noted that as used herein and in the appended claims, the singular forms “a”, “an”, and “the” include plural referents unless the context clearly dictates otherwise. Thus, for example, reference to “the system” includes reference to one or more systems and equivalents thereof known to those skilled in the art, and so forth.

Various approaches have been previously disclosed to create a planar dissection at a defined depth below the dermis. In one approach, as described in U.S. Pat. No. 10,271,866, the entire contents of which are incorporated herein by reference, a plane of dissection may be created generally parallel to and at a predefined depth below the dermis or may be created at an angle or in a curved shape relative to the surface of the dermis. The disclosed device and methods are additionally described as being used to enlarge the tissue pocket created by the dissection by applying a vacuum assisted suction force during the performance of the dissection and lifting the skin after the dissection is completed. Application of vacuum on the skin during the dissection process may put traction on the underlying tissues, may better align the fibrous septa for dissection with the cutting tool, and may allow for uniform and instantaneous separation of the dissected tissue layers. In one aspect, vacuum can be created thermally such as accomplished in a cupping procedure where a flame or other heat source is employed. In an alternative novel approach, in addition to suction or in place thereof, adhesive is used to lift skin during the performance of dissection and lifting the skin after dissection is completed.

Figure 1B:
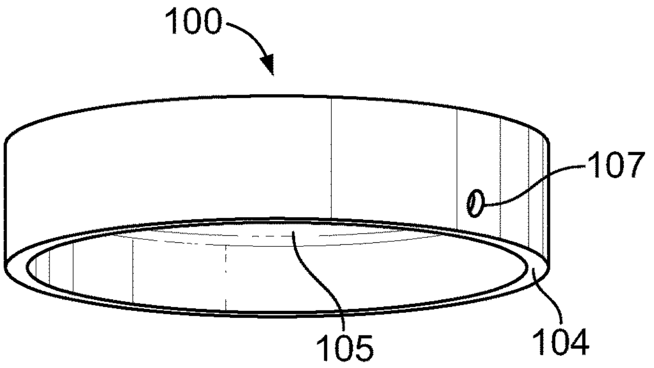

As illustrated by FIGS. 1A-B, the prior approach describes utilizing a handpiece 100 to capture and control a location of the skin, or dermis 101, as well as precisely control use of a cutting tool 102. The handpiece preferably has a top 103 and a perimeter elevation 104 that cooperatively define a recessed area 105 which can be placed over the patient's skin. By applying a force to the top of the handpiece or by a vacuum supplied to the handpiece, a portion of the dermis 101 can be moved into the recessed area to substantially fill the recessed area, thus capturing it within the handpiece and providing some control over the area of tissue captured. This allows a distal portion of cutting tool 102 or other suitable dissection device to be inserted through a conduit 107 extending through a side of the perimeter elevation of the handpiece, percutaneously through the tissue disposed in the recessed area, and into the subcutaneous tissues encompassed by the recessed area of the handpiece. Cutting tool 102 is maneuvered in such a way as to cut a surgical lesion of a predetermined shape inside the subcutaneous tissues within the recessed area and parallel to the top of the handpiece. The surgical lesion (i.e., dissection) is targeted to be in a range from as shallow as at 1 mm to 2 mm below the interface between the dermis and the shallow fat, to as deep as 20 mm below the skin/fat interface. It is to be recognized that the cutting tool 102 can in an alternative or additional embodiment be configured to operate as a fluid delivery component such as for anesthesia.

Figure 1C:
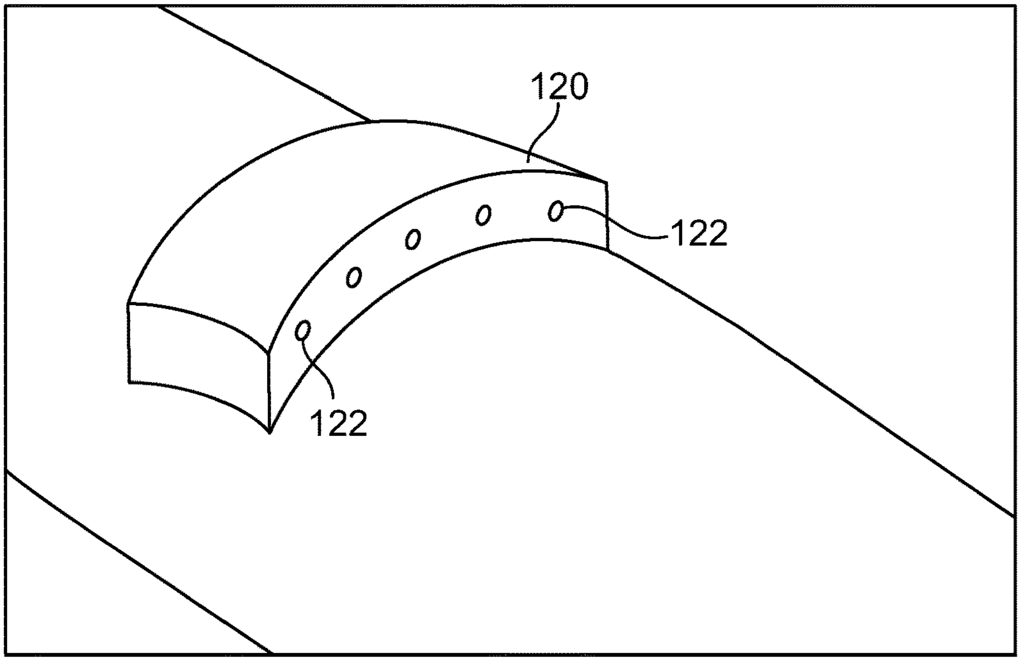
FIGS. 1C-H depict alternate approaches to handpieces and cutters of a dissection device.
Figure 1D:
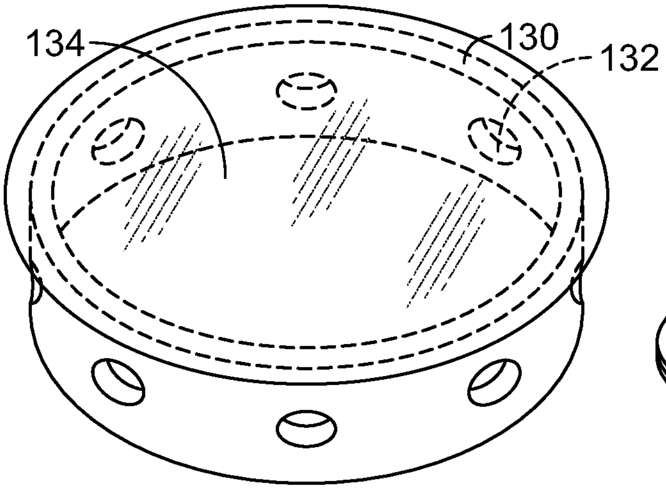
Figure 1E:
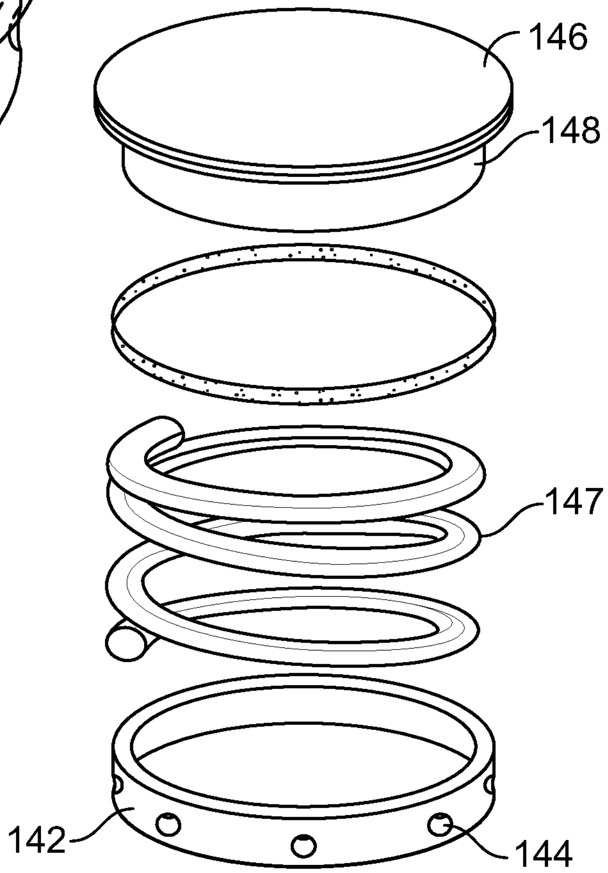
Figure 1F:
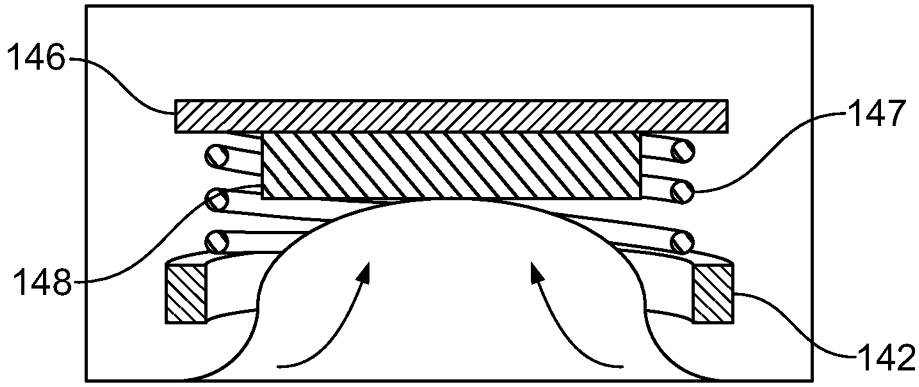

With reference to FIGS. 1C-G, in alternative approaches, the handpiece can assume other configurations and can be made from material that adapts to the shape of the tissue surface to which it is applied. For example as shown in FIG. 1C, curving to match the thigh to which it is applied. A kit of various sized and shaped handpieces can be provided for a particular treatment procedure and thus provide location specific structures. Additionally, by planning ahead, the handpiece can be formed of a perimeter that can change shape for a specific procedure, such as being formed from telescoping, pivoting, adjustable or moldable, customized (e.g. 3D printed) or segmented materials. For example, as shown in FIG. 1C, rather than defining a circular shape, the handpiece 120 is a generally rectangular structure that is bendable to conform to the tissue targeted for treatment. The handpiece can additionally include a plurality of conduits 122 through which a cutting tool or other treatment device can be inserted. In this way, the fractionalization of a targeted area can be templatized. A lower side of the handpiece 120 can be configured with an adhesive for lifting tissue or the handpiece 120 can be attached to suction for accomplishing lifting tissue. Moreover, in another approach (FIG. 1D), the handpiece 130 defines a ring structure and includes a plurality of conduits 132 through which the cutting or other tools can be inserted to accomplish desired treatments within the ring structure itself or within an interior 134 of the ring 130. A clear lid is configured over the interior 134. Suction and/or adhesive can be employed to lift tissue when using the handpiece 130.

In yet a further approach (FIGS. 1E-F), a handpiece assembly embodies a ring-like base 142 including a plurality of conduits 144 formed therein as well as a spring-loaded top 146 sized and shaped to be received within the base 142. A spring 147 is configured between the top 146 and base 142. A lower platform 148 of the top 146 can be equipped with an adhesive to engage and lift target tissue. When lifted, a treatment and/or cutting tool 107 is inserted through one or more of the conduits 144 to treat target septa. The extent to which the top 146 is lifted with respect to the base 142 is controlled by the springs 147. Various different heights between the top 146 and the base 142 can be provided by structure such as that provided in a ball-point pen.

Figure 1G:
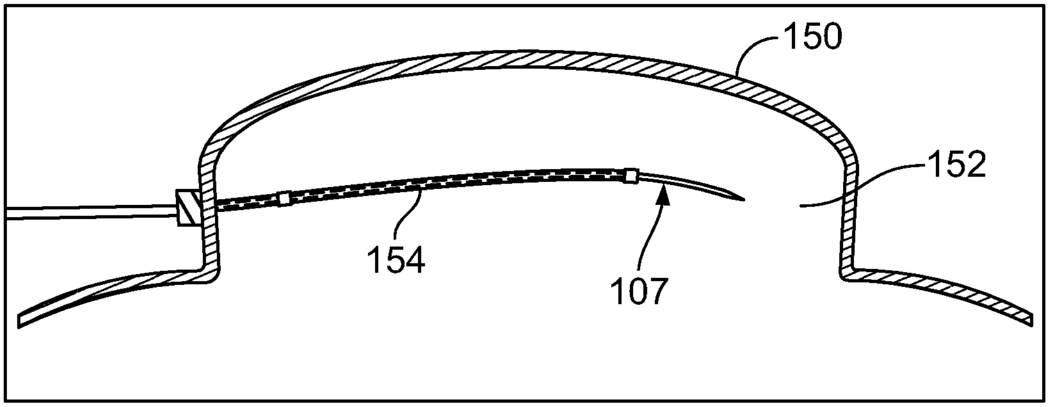
Figure 1H:
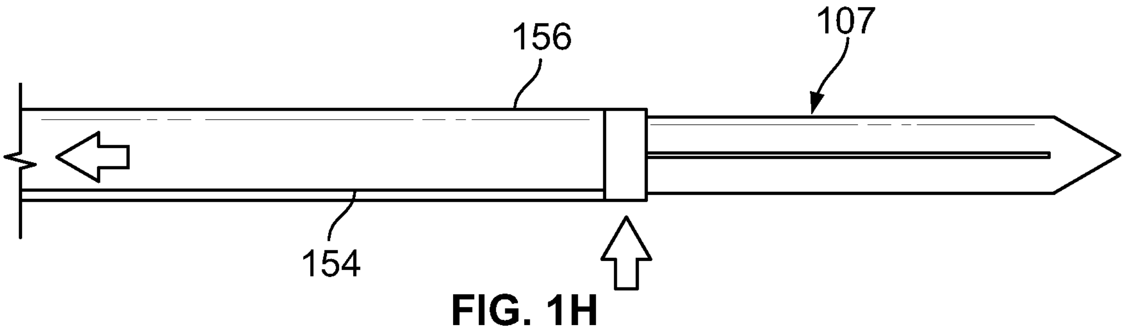

With reference now to FIG. 1G, there is shown a handpiece 150 having a curved chamber 152 through which a cutting tool 107 can be inserted. To navigate within the curved chamber 152, the cutting tool 107 is equipped with one or more steering wires 154 configured to deflect the cutting tool 107 to reside in various positions. Such steering wires 154 can be operator controlled or involve smart tensioning so as to counter bending forces and make a relatively small diameter device seem stiffer than would be provided by its structure alone. Here, the tensioning/steering wires 154 are linked to the advancement of the device so that an appropriate amount of curvature is introduced based on the location of the cutter 107 within the chamber 152. Moreover, the stiffening of the device at the cutter 107 can be responsive to forces experienced at the cutter 107 such as those associated with engaging septa. For example, the stiffness of the assembly is increased or decreased as necessary, automatically or manually, when navigating through the chamber and when engaging septa targeted for cutting. In this way, the assembly also can be used to identify target tissues. As shown in FIG. 1H, the cutter 107 is provided with a steering sheath 156 the operation of which can also be operator manually controlled or automatically controlled by a computer. The sheath 156 is configured to steer the cutter 107 and to create a relatively thin device with an active stiffness for cutting. It is to be recognized that such steering functionality can be incorporated into any of the disclosed cutting or treatment devices.

The handpiece and/or other components of the treatment system can also be custom fitted or manufactured or 3D printed to match the target treatment surface of the patient and/or a treatment plan developed for a patient. In this way, the handpiece for example can be best form fitted to a treatment surface so that an effective seal is made between the handpiece and tissue. Moreover, the number of incisions into tissues can therefore be minimized through such individualized treatment structures. Various sealing structures such as o-rings or flexible perimeters can also be provided along the surfaces where the treatment device engages tissues. In yet another approach providing for individualized treatment, the cutting tool can first be placed through skin and within the treatment site followed by applying suction or other means for lifting tissue so that treatment need not be constrained by the prior placement of the handpiece. This approach is aided by the transillumination structure disclosed below. Moreover, compression bands (not shown) can be applied at or near treatment sites to cause tension in uncompressed areas for the identification of target septa or to add in tensioning target septa for treatment. In this context, a physician presses or a device is used to push down on one area of skin and the displaced tissue causes an increase in tensioning of septa in nearby areas to thereby facilitate the identification of cellulite, and also to aid in accurately controlling treatment depth.

Figure 2A:
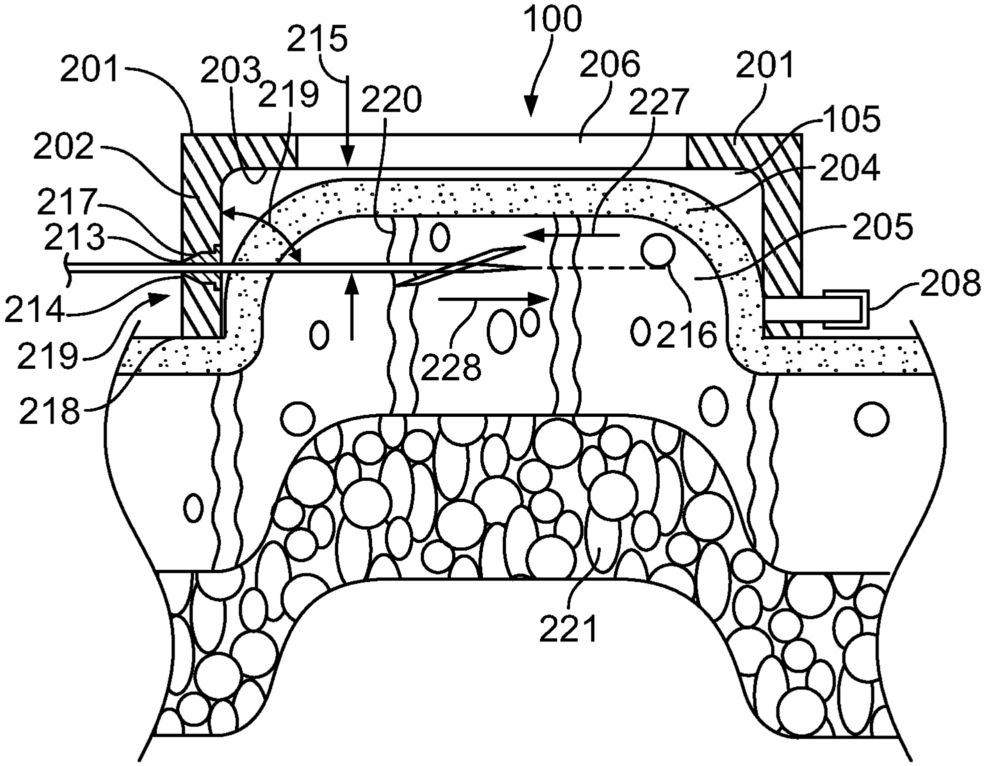
FIGS. 2A-B depict a cut-away view and perspective view of the handpiece of FIG. 1 in conjunction with a cutting tool.

As shown in FIG. 2A, in previously disclosed approaches, a top wall 201 and perimeter wall 202 define a tissue apposition surface (tissue facing surface) 203 facing into recessed area 105. Tissue apposition surface 203 may be curved inward to the handpiece, or concave, or recessed, so that when handpiece 100 is disposed against an epidermis 204, further pressure against the handpiece 100 will cause the handpiece to encompass a subcutaneous level of tissue 205, particularly the subdermal tissue layer below the epidermis and dermis layers, wherein these layers will be positioned within recessed area 105. A tissue apposition surface 203 can include a perimeter wall 202 as a relatively small inner wall around the perimeter of recessed area 105 and handpiece 100 may include a transparent cover 206 so that a physician can clearly see and verify that the dermis is properly positioned within the dissection region.

In use, the disclosed device 100 is pressed against the tissue to move the subcutaneous layer 205 into recessed area 105 and against tissue apposition surface 203. In some embodiments, vacuum (suction) is used to enhance the capture of the tissue. As stated, in additional or alternative embodiments, adhesive is used to capture tissue. Where suction is employed, a vacuum source may be placed in fluid connection with handpiece 100 via an optional vacuum port 208 on handpiece 100. The vacuum source may include a vacuum pump in fluid communication with recessed area 105. Vacuum pump supplies suction to the recessed area to pull tissue snugly and securely therein. In some embodiments, the vacuum pump is configured to communicate with a microprocessor and the graphical user interface to display a vacuum pressure. The system may further include a display indicating the elapsed amount of time vacuum was supplied to the handpiece by the vacuum pump. The vacuum pump may also modulate the suction such that a higher suction force is applied initially to pull the tissue into the recess, and a somewhat lower suction force is used to maintain/hold the tissue in place thereafter. In other approaches, suction can be provided by a syringe configured to pull the desired vacuum on the skin to tension the septa or otherwise lift skin. Cupping structures or other vacuum providing bellows can also be incorporated into a suction device that provides the desired suction.

Figure 2B:
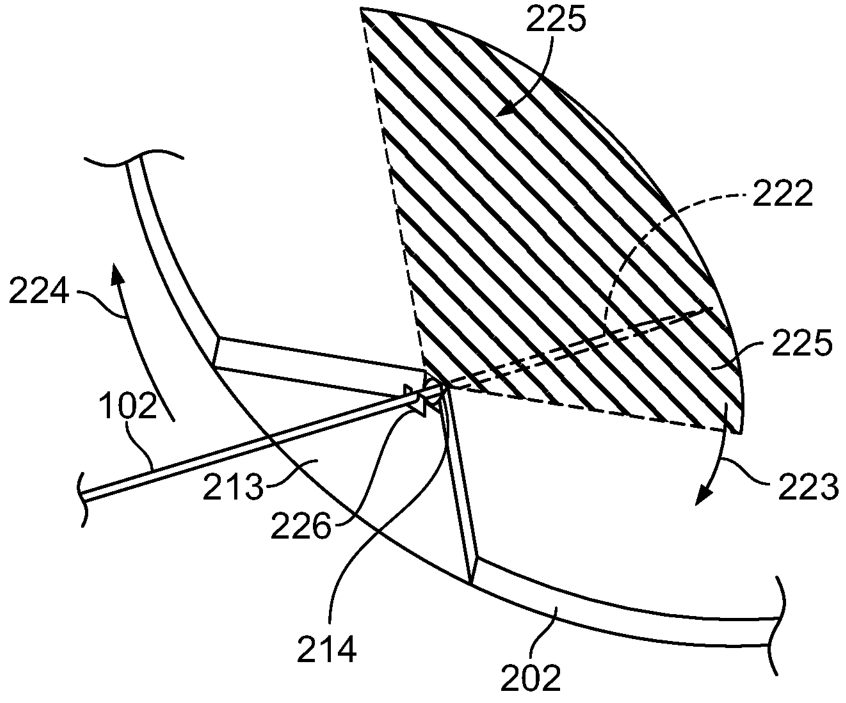

Suction applied at vacuum port 208 causes skin 101 to be pulled up into contact with apposition surface 203 of handpiece 100. By applying a sufficient suction force, a portion of epidermis 204 is pulled into the chamber of vacuum handpiece 100 and conforms to inner recessed area 105. While the surface of the skin 204 is tightly positioned against top wall 201 and perimeter wall 202 of recessed area 105, fat layer 205 (subcutaneous tissue) is also drawn into the chamber. A cutting tool 102 (e.g., a cutting blade or RF probe, or needle), can be inserted through a conduit 213 in a side of handpiece 100 and through entry hole 214, through the skin, and into the subcutaneous tissue. The blade can assume various configurations including curved and angled surfaces and profiles, as well as a serrated configuration of various sizes, shapes and lengths. Moreover, the blade assembly can be embodied one or a plurality of horizontally extending blades that reciprocate longitudinally or perpendicularly to the direction the horizontally extending blades extend, and with respect to one or more stationary, or independently reciprocating, horizontally extending members or blades (such as in a clipper or hedge trimmer). Significantly, the handpiece enables the cutting tool to be consistently inserted at desired treatment depth 215. Handpiece 100 thus provides for precise control of the depth of the dissection plane and allows for cutting and/or movement of tool 102 substantially parallel to the surface of the tissue along a plane 225 (FIG. 2B). Moreover, notably, use of an RF probe device or other energy emitting device in combination with or in place of a reciprocating blade lends itself to the electrocauterization of target tissue and septa.

A membrane 217 formed of a flexible and resilient material may also be applied to the perimeter wall (sidewall) across the proximal (away from the recessed area) or distal ends (closer to the recessed area) of the conduit 213 to minimize vacuum leakage there through. The membrane 217 preferably is sufficiently resilient to seal around the cutting tool as it pierces (self-sealing) therethrough and minimize vacuum leakage. Membrane 217 may be formed of silicone.

Conduit 213 is preferably located proximate a bottom edge 218 of perimeter wall (sidewall) 202 to allow a cutting tool or needle to be inserted into the tissue (captured in the recessed area) in a plane parallel to the dermis. Conduit 213 supplies an angle of penetration 219 so that the tool inserted through the conduit will penetrate into tissue disposed within the recessed area, and substantially parallel to the surface of the tissue and parallel to the surface of top wall 201 at depth 215. As depicted in FIG. 2B, entry hole 214 is preferably disposed on an inner side of the conduit and facing the recessed area. Conduit 213 preferably widens outward toward an outer side of the perimeter elevation such that a distal end 222 of the cutting tool inserted through the entry hole moves in one direction 223 when a proximal end of the cutting tool outside the conduit moves in an opposite direction 224. Entry hole 214 thereby defines a cutting tool pivot point when a distal end 222 of cutting tool 102 is inserted through conduit 213 and into recessed area 105, and the tool moves primarily in an x-y plane 225 parallel to the top surface of the handpiece. In an alternative approach, the cutting tool pivot point is configured to reside within tissue so as to minimize trauma to the tissue insertion entry point. In some embodiments entry hole 214 may include an optional locking mechanism 226 that locks the tool in place upon insertion into the conduit. In some embodiments in which a vacuum is supplied to the recessed area, an optional gasket or seal 217 (not shown in FIG. 2B) may be placed within, in front of, behind, or around entry hole 214 to minimize vacuum leakage.

Figure 3A:
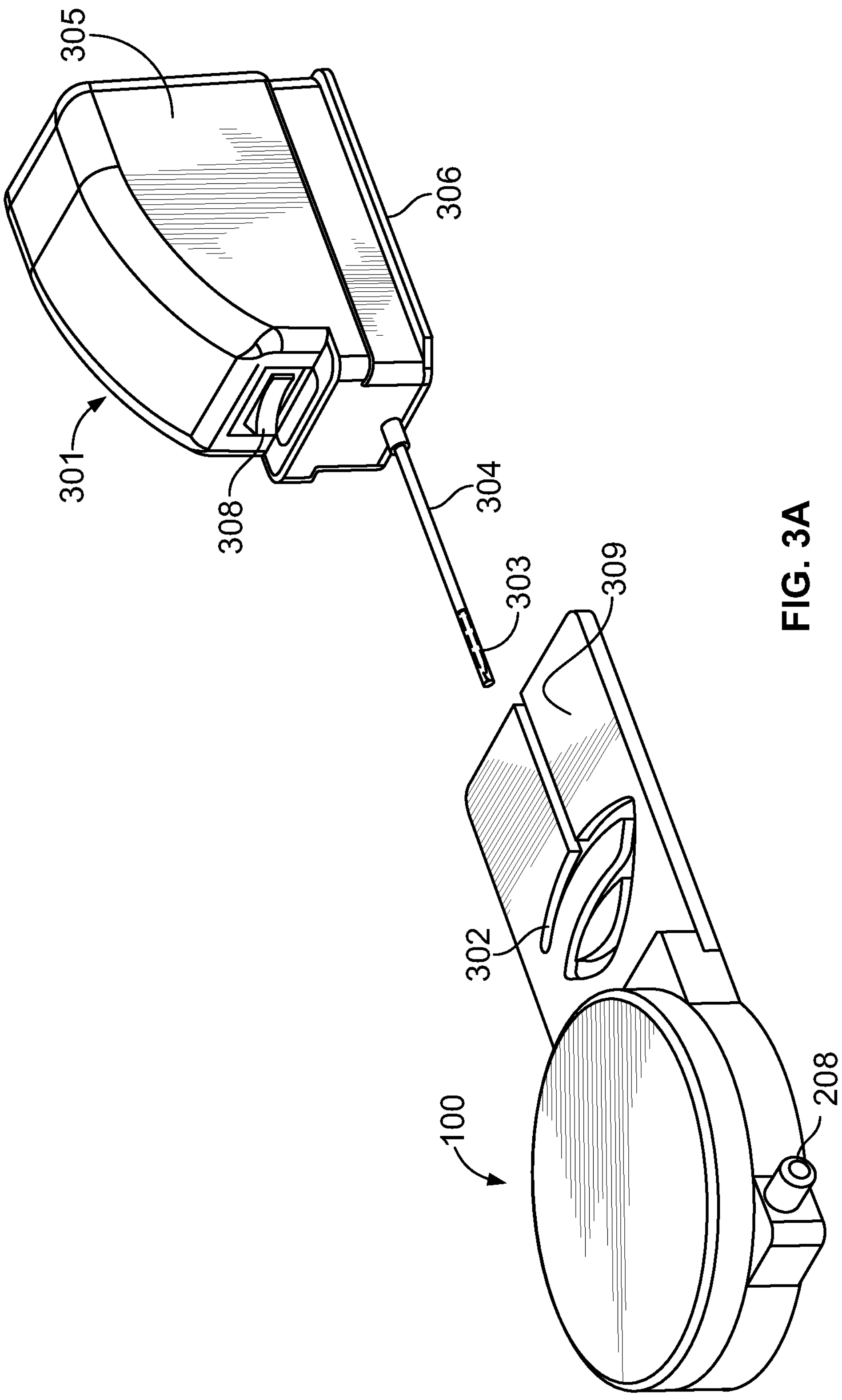
FIGS. 3A-B depict a perspective view of the handpiece and motor controlled cutting mechanism.
Figure 3B:
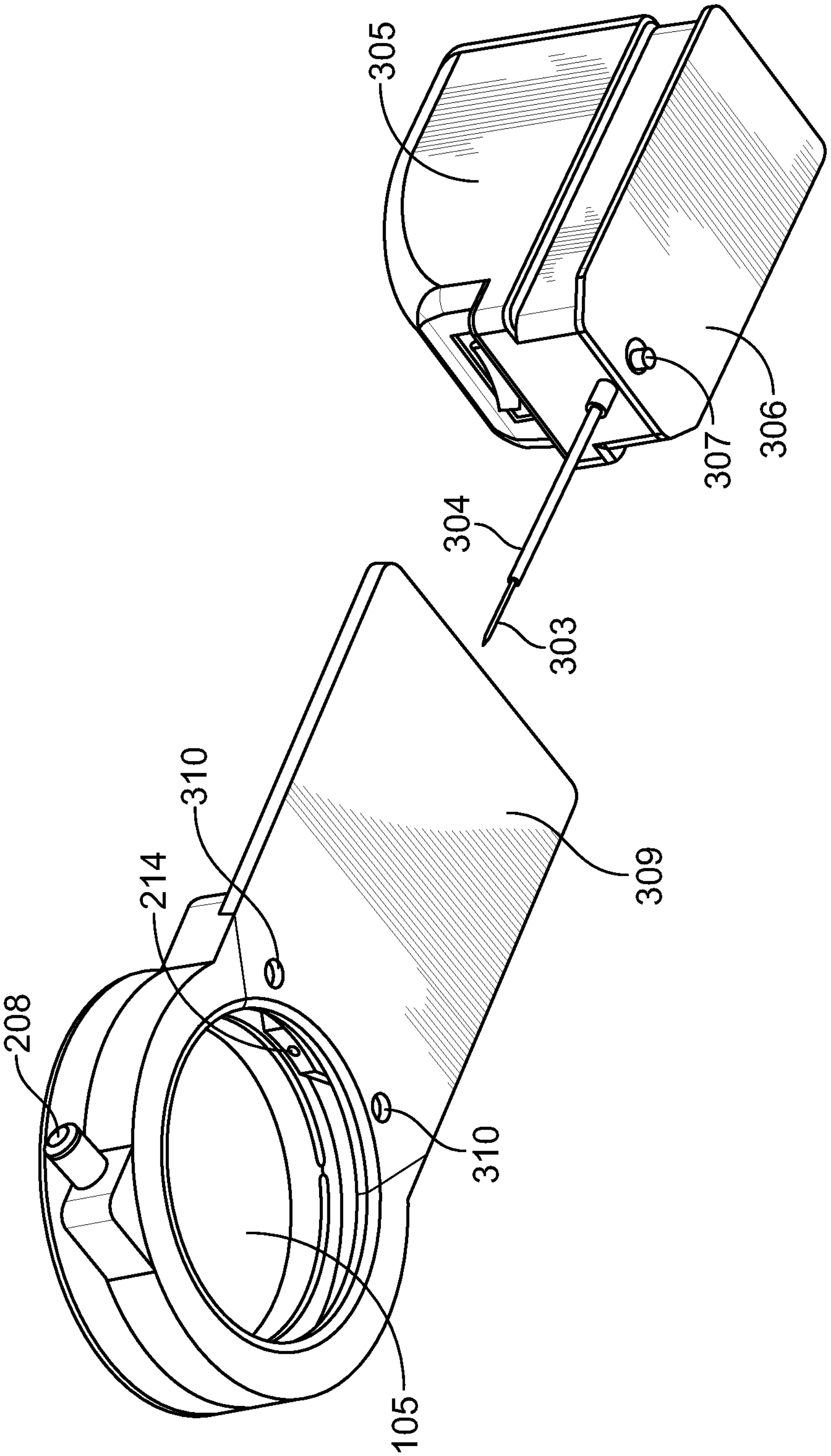

As depicted in FIGS. 3A and 3B, the previously disclosed dissection system includes a motor controlled cutting module 301 and a guidance track 302 operably connected (i.e. physically and/or via sensing) to handpiece 100. In one embodiment, the motor module 301 is configured so that its operation is controlled by its interaction with the guidance track 302. That is, the motor commences manipulation/reciprocation of a cutting device only once the cutting device is placed within tissue and at the treatment site. The motor then ceases its action once the cutting device is removed from the treatment site within tissue. Thus, the tool insertion point is protected from an active, reciprocating or other blade by shutting the motor off. In one approach, the base or guidance track can include a switch that automatically turns the device off in the event the cutting tool is removed from the guidance track or platform along which the treatment device is passed. The switch can be triggered in the pathway provided by the guidance track or platform such that the device will only turn on or off when positioned in a prescribed pathway or position. Where the device is not provided with a guidance track, the platform along which the device is advanced can be provided with sensing and control provided by a photo diode or a magnetic surface and tool sensing arrangement. Accordingly, such a platform can be color coated and the photo diode responds to the color it passes over such as turning on when detecting green and turning off when detecting red. Colors or color intensities can also be provided on a platform for controlling speed of reciprocation or other action (opening and/or closing) of the cutting portion of a treatment device. Further, the cutter module includes an embodiment of cutting tool (a reciprocating cutting blade 303 disposed in a retractable and advanceable sleeve 304) and a housing 305 and a base 306. Guidance track 302 is generally configured to constrain a portion of the cutting module guide pin 307 in contact with the guidance track to move along a predetermined path. This guide pin 307 can be utilized through its localization with respect to the guidance track 302 to control operation as stated above, that is, turning the motor on and off when the cutting tool 102 is positioned within tissue and at the interventional site. Thus, a distal end of the cutting tool, passing through entry hole 214, cooperatively moves within recessed area 105 in a plane substantially parallel to the top of the handpiece and within a region of a predetermined shape defined by the predefined path. Motor operation of cutting module 301 is preferably controlled manually by an electric switch or button 308, but may also be activated by electrical or other contact means known in the art within the guidance track.

Figure 4A:
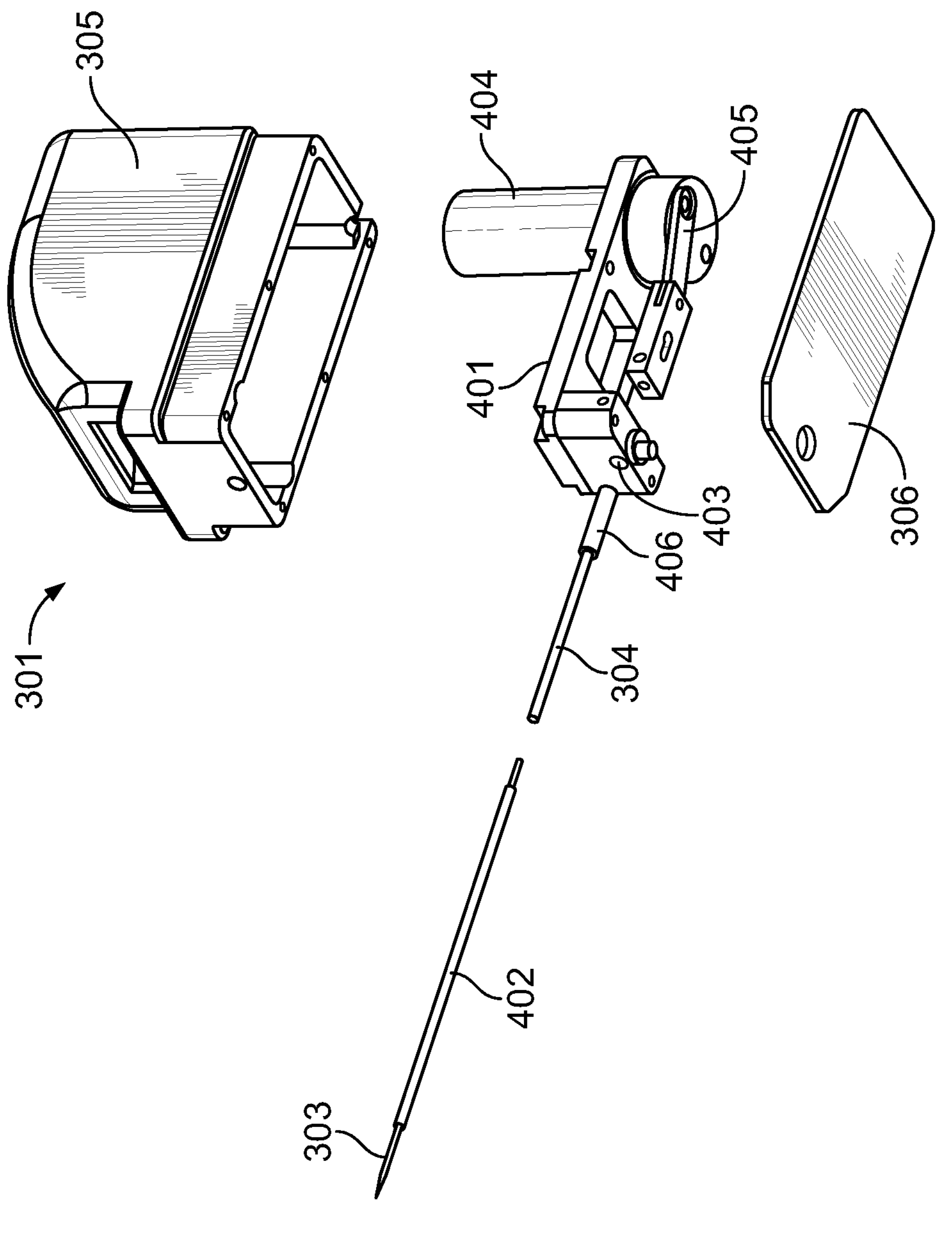
FIG. 4A is an exploded view, depicting the motor controlled mechanism.

FIG. 4A depicts an exploded view of the previously disclosed cutting module 301. Cutter module 301 includes housing enclosure 305 and base 306, motor assembly 401 mounted on the base and enclosed by the housing, and a reciprocating cutting blade 303 operably connected to motor assembly 401. Cutting blade 303 is slidably disposed within sleeve 304. Sleeve 304 minimizes the amount of tissue in direct contact with the shaft 402 of the cutting blade 303 to minimize drag and or tugging on the tissue. Sleeve 304 also enables the isolation and/or capture of any fluid that may travel along the shaft of blade 303.

A motor assembly 401 is enclosed in enclosure 305 and base 306. Sleeve 304 is affixed at a distal end 403 of motor assembly 401. In one embodiment, motor 404 is a DC motor which may incorporate a gear reduction. In the depicted embodiment, a crank slider 405 converts motor rotation to cutter reciprocation. Motor 404, within enclosure 305 moves reciprocating cutter blade 303 within sleeve 304. As the motor turns, crank slider 405 moves cutter 303 back and forth within sleeve 304. Cutter blade 303 may include a needle or a bayonet which may further include one or more sharp edges.

Sleeve 304 does not reciprocate and is typically comprised of a thin-walled polymer tube and is sterile for single patient use. In one particular embodiment, the sleeve 304 can be configured to be selectively translatable over the cutter blade 303 so that it can protect the tissue from the cutter blade 303 when desired, such as when entering tissue or between treatment sites (See FIG. 3A), and also at the incision site during cutting within tissue layers. Sleeve 304 and cutter blade 303 are typically disposable. Sleeve 304 may be affixed to cutter module 301 (and/or crank slider 405) by means of connection point 406. Connection point 406 may be a disposable protective connector keeping cutter module 301 and gear motor assembly 401 in fluid isolation from sleeve 304 and cutting blade 303. In this manner, cutting blade 303 and sleeve 304 could be disposed along with connection point 406 after each procedure. Correspondingly, cutting module 301 including motor assembly 401 and base 306 could be reused in subsequent procedures.

With reference again to FIGS. 3A and 3B, the handpiece also preferably includes a platform 309 integral with or affixed to a proximal side of handpiece 100. Platform 309 preferably includes guidance track 302, wherein guidance track 302 is used to position, guide, and support cutting module 301 by means of a guide pin 307. Guide pin 307 moves within and along the path of guidance track 301 to stabilize the cutter module at a proper position proximate to handpiece 100.

In this embodiment, guide pin 307 protrudes through base 306 of cutter module 301, however, in other embodiments guide pin 307 may be part of base 306 or cutting module 301. The guide pin may serve dual purposes. Guide pin 307 serves to guide the disclosed cutting module embodiments to create a surgical lesion defined by the path of guidance track 302. Additionally, the guide pin may include a feature such as an enlarged head or the like which interacts with guidance track 302 and prevents cutting module 301 from being lifted off the platform 309 and/or supports cutting module 301 at a predefined planar orientation relative to platform 309.

A physician treating the patient determines an instrument insertion site and paths that most efficiently treat cellulite with a minimal amount of insertion sites and instrument paths under the skin. Preferably, an instrument insertion site is chosen that is in a crease or fold of skin such as where the buttocks meets the thigh or in the crease between the two buttocks at a location that is not seen when the buttocks are in natural contact for improved cosmesis after the procedure healing period. In certain patients, the inner thigh is chosen as an insertion site as this location is less visual as it heals. Such treatment paths are selected by the operator or can be generated automatically by employing a computerized controller programmed to most efficiently address and measure cellulite residing in a pre-defined treatment site. Thus, the treatment device can be programmed to take any possible or conceivable path or pattern of treatment.

The computerized controller can be associated with a scanner or camera that identifies specific dimples and areas for treatment such as by employing laser technology. In this regard, the computerized controller includes a program specific to cellulite treatment and is used in conjunction with an electronic and mechanical device and comprises or includes a non-transitory computer-readable storage medium and a computer-program mechanism embedded therein to both identify treatment areas and to plot primary and alternative approaches to treatments. In another embodiment, computerized visualization and treatment planning equipment is used to assist the physician in determining insertion site locations and paths to be taken to the marked targets.

Figure 4B:
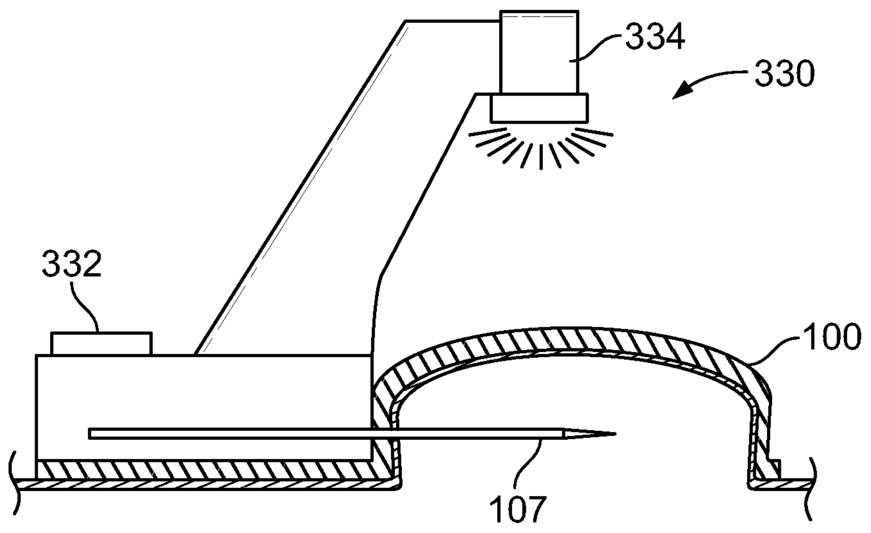
FIGS. 4B-C, are top and side views, depicting a treatment system incorporating a camera.
Figure 4C:
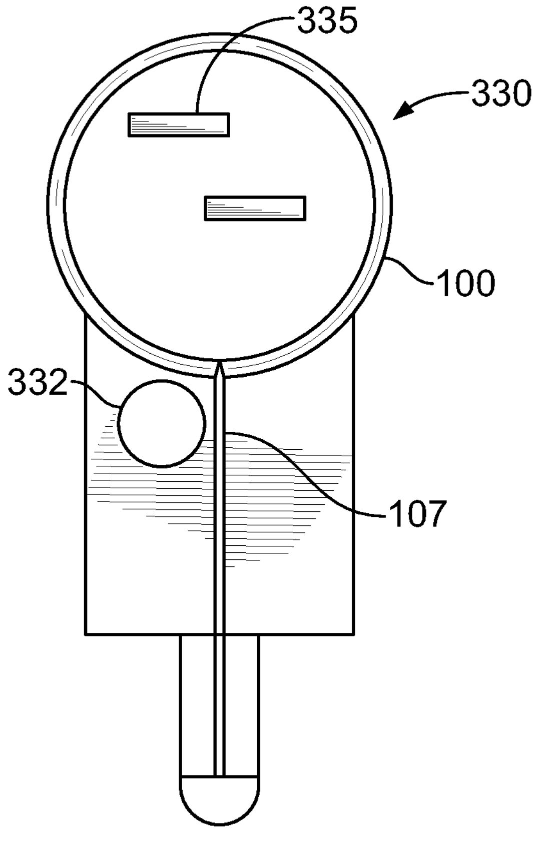

In one approach (FIGS. 4B-C), a treatment system 330 includes a pressure gauge 332 associated with the system computer, the pressure gauge 332 being operatively associated with the performance of the treatment system such that treatment can only be performed when the system confirms that sufficient vacuum is being applied to the treatment area. Further, as shown in FIGS. 4B-C, the treatment system 330 additionally includes a downward facing digital camera 334 configured to see marks 335 associated with pre-determined treatment locations viewable through a transparent handpiece 100.

The camera 334 communicates with the system computer and the system computer determines the treatment approach based upon the images provided by the camera. Accordingly, a user need only place the treatment system over a treatment site marked for treatment and instruct the system to begin operation, such as through the pushing of a button. Once the required suction forces are confirmed, the camera 334 communicates with the system computer to follow the plan of treatment. Thereafter, with or without further operator input, the system then automatically proceeds with treatment. The assembly is then moved to additional treatment sites as necessary.

During treatment, the patient lies down on their stomach on the treatment table. Alternatively, because of the minimally invasiveness of the current approach, a patient can be treated while standing, particularly for a small number of treatment targets, or while standing and leaning forward on a support and alternatively between standing and leaning forward so that gravity can help identify and confirm treatment of the targeted septa. Moreover, a measurement device such as a camera and system computer, creates a complete three-dimensional map of all cellulite relative to normal skin. By dating and comparing improvement of volume of divots or dimples versus normal idealized surfaces, the operator calculates total and local volume benefits of therapy and track improvement over time.

In one specific alternative approach, treatment can be directed at various positions about connecting tissue or septa. That is, septa can be engaged, stretched, re-oriented, torn, cut, sliced, ruptured or disrupted from various sides or angles respecting septa and the treatment target location. Thus, septa can be treated from superior, inferior or medial or lateral locations from the septa and treatment target location to achieve the best results. For example, in a particular situation, treatment can be most effective from a position superior on the patient above a particular connecting tissue to take advantage of gravity where treatment forces placed on the connecting tissue coincide with the direction of gravity or the direction that gravity most often works on a standing body, as it has been observed that cellulite is often most visible in a standing individual.

A force gauge (electronic or mechanical) can be provided to ensure that a pre-determined amount of force would be applied to the tissue when testing the septa to prevent over or under pulling. A treatment device capable of one or more of engaging, stretching, slicing, cutting or disrupting connective tissue is configured at a distal end portion of the device. All cutting means can be combined with or further energized with RF, a laser, ultrasonic or thermal energy to produce cutting and coagulation together or separately. In certain aspects, there can be a single entry site or two entry sites, one high on the hip and another along the crease or transition between the buttocks and thigh, or at the inner thigh. Such locations are characterized in that they can be easily hidden either naturally or by clothing. Treatment targets, depressions and dimples that have been marked on the skin surface while the patient is standing often go away when the patient lies down on their stomach because gravity acts on the skin and underlying connective tissue in a different direction such that the ink mark is apparent but the dimple or depression is not. Interventional devices are configured such that a user can approach a target location and first use the interventional device to push, pull or otherwise tension septa in a target area under the skin to identify the specific septa impacting the target location and/or which is the cause of the expression of cellulite. In other words, pulling or pushing on the septa under the skin to find the one(s) that create the dimple or depression in the skin surface. For some treatment targets, taking an approach from an entry located inferior the treatment target, advancing the end of the interventional device with a hooking and cutting element beyond the treatment target and then extending the hooking and cutting element and pulling inferiorly (effectively the "down" direction if the patient was standing) can provide a better approach in locating septa. For some treatment targets, taking an approach from an entry located superior the treatment target, advancing the end of the device with the hooking and cutting element collapsed beyond the treatment target and then pulling superiorly can provide an alternative effective approach (for example, for treatment targets on the leg, to re-create the dimple when the patient is lying down). One or more strain gauges can be incorporated within the treatment device to help identify target septa as well as to assess the progress and completion of treating septa. This facilitates targeting of key septa in a less impactful way, ideally minimizing bruising or other issues associated with cutting or disrupting a large area around the target. There are thus herein shown various approaches to treating cellulite expressed as dimples or depressions in the skin surface. Moreover, the handle portion can be employed to create an indentation in skin through which interventional devices can be inserted subcutaneously. A treatment regimen is selected for inserting interventional instruments based upon the subject's anatomy as it relates to the septa connecting tissue layers that define the chambers retaining fatty or other tissues. If desired, while anesthetic and/or sedation is taking effect, ultrasound can be used to assess the subcutaneous trajectory and depth of the various connective tissue bands responsible for the surface unevenness. The ultrasound evaluation can help with the particular trajectory selected for the desired depth. The ultrasound evaluation can also help with positioning the distal end portion of the treatment instrument strategically at the connection point between the connective tissue and the dermis or the facia.

Figure 5:
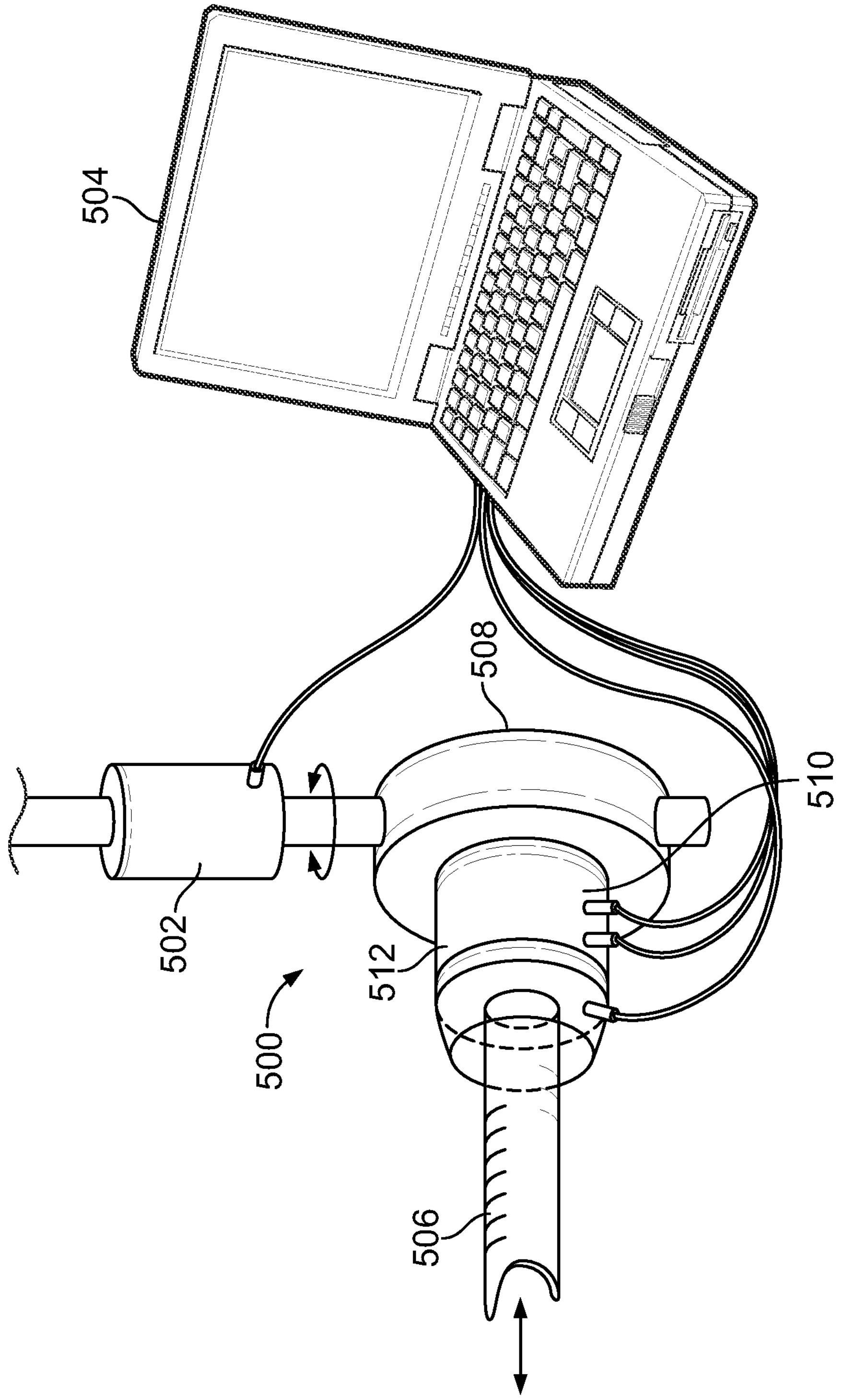
FIG. 5 is a perspective view, depicting a tool control mechanism.

In an additional or alternative embodiment, a tool control mechanism 500 (See FIG. 5) is provided which allows cutting tool or other tool appropriately configured device, to be controlled by a microprocessor. In one or more embodiments, the microprocessor controls cutting device, with or without manual assistance of the operator, to precisely cut an area of tissue disposed within a recessed area of the handpiece. The area being cut is predetermined and programmed into the microprocessor by the operator of the handpiece. Various areas and patterns of treatment can be achieved as desired and required for a particular patient.

In one approach, the tool control mechanism 500 includes a motor assembly 502 controlled by a programmable controller 504 and one or more of lateral and axial movement of the treatment device is controlled. The motor assembly 502 drives a shaft 506 configured to pass laterally through a bushing 508. An optical encoder 510 is configured axially within the bushing 508, and a clamp 512 is attached to the optical encoder 510. Both the optical encoder 510 and the clamp 512 are also controlled by the controller 504. Communication with the controller 504 can be wireless or via a hardwire connection with one or more components. The clamp 512, optical encoder 510 and bushing 512 are aligned and include a through hole sized and shaped to receive a shaft 506 of a cutter device, the shaft 506 being marked in a manner to communicate with the optical encoder 510. Here, the user will have control of advancing the cutter or other interventional device within the tool control mechanism 500 but a second automatically controlled motor (not shown) can be incorporated into the assembly to control longitudinal motion of the interventional device as well. In use, the controller 504 is programmed for treating a patient with a specific treatment regimen. Once the patient is prepared for the interventional treatment, the user or second motor will advance the interventional device within the bushing 508 and the controller 504 will turn the bushing 508 as directed by the treatment regimen and based upon the optical encoder readings. The controller 504 monitors the optical encoder 510 as it identifies the shaft 506 markings to determine the depth the interventional device assumes. The controller 504 simultaneously controls the clamp 512 based upon the position of the shaft 506 and stage of the pre-programmed treatment. In this way, a controlled and precise treatment can be achieved by the tissue treatment system.

Figure 6A:
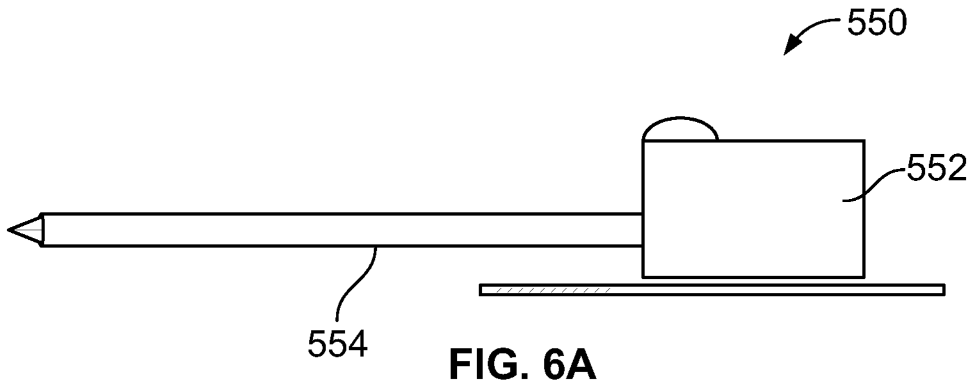
FIGS. 6A-F depicts an alternate approach to a treatment system.
Figure 6B:
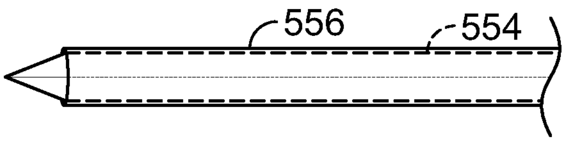
Figure 6C:
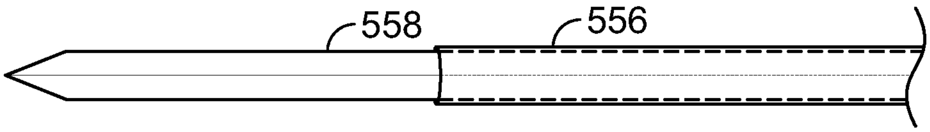
Figure 6D:
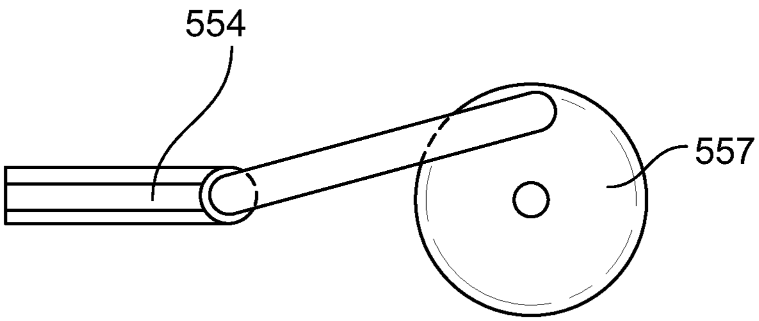
Figure 6E:
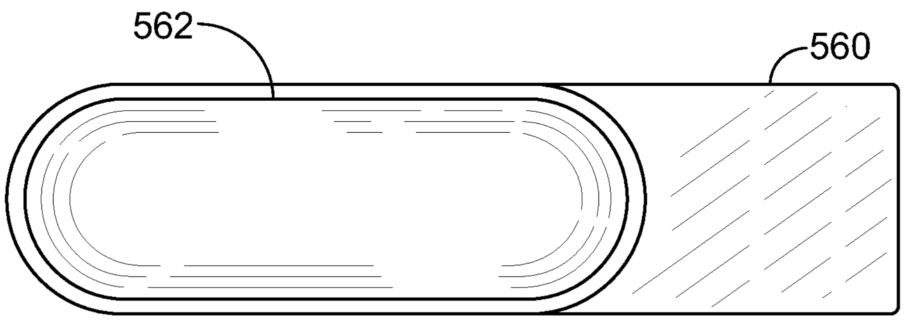
Figure 6F:
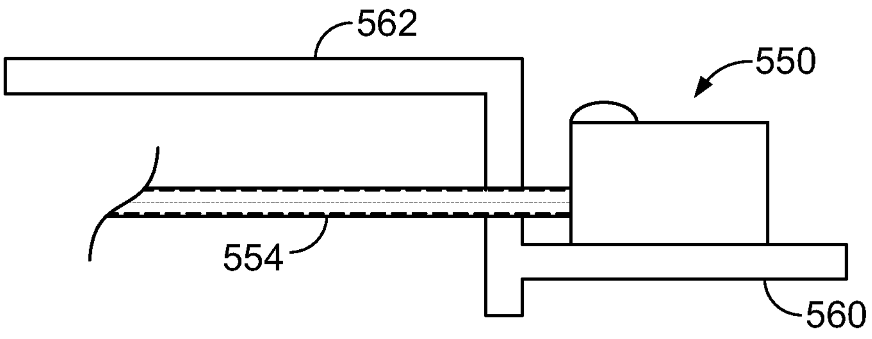

Turning to FIGS. 6A-F, another approach to a treatment system 550 is presented. The treatment system 550 includes a base unit 552 and an elongate member 554 extending from the base unit. As best seen in FIGS. 6B-C, the elongate member 554 is equipped with a retractable sheath 556 selectively covering a cutting device 558. Here, the cutting device 558 is shown as a double edged blade, but any of the disclosed embodiments of cutting structures can be used. Notably, as described herein, the sheath 556 can be operator or automatically computer controlled so that the sheath 556 covers the cutting surface of the cutting device 558 when desired such as when the elongate member 554 is outside a patient's body and/or navigating within tissue or when not being employed for cutting. Accordingly, proximally extending wires or other elongate structures are attached to the sheath 556 to control its positioning. Housed within the base unit 552 is one or motor assemblies for controlling the operation of the cutting device 558 and/or sheath 556. As shown schematically in FIG. 6D, one embodiment of a motor assembly 557 for creating reciprocating motion of the cutting device 558 can be utilized. This motor assembly 557 can be battery powered or connected to an outside power source. In one aspect, engaging the motor assembly 557 can simply cause the motor to spin and allow the cutter 558 to advance out of the sheath 556 to accomplish required cutting. The length of the exposed cutting surface of the cutting device 558 can be set by altering the oscillating structure of the motor assembly 557. In another aspect, an on button can be used to power the system, releasing of the same would cause the system to power off. A treatment platform 560 and a receptacle 562 are further provided, the receptacle being attached to a suction force or includes an adhesive for lifting tissue within the receptacle 562 (FIGS. 6E-F). Notably, the receptacle 562 can assume any one of a number of shapes and configurations, and can include a seal (such as a membrane placed within the receptacle 562) through which the cutting device 554 is inserted. The receptacle can be sized and shaped for use on the buttocks and/or the thigh, and can be formed as a single molded part with a co-molded or second molded material creating an elastomeric edge for flange for sealing and/or comfort. Additionally, the platform 560 is characterized by a smooth surface along which the base unit 552 can be slid. Here, no tracks are provided to constrain the movement of the base unit 552 and thus the cutting device 558 can be moved as desired within a treatment site also without constraint, and the treatment site can be as large or small as is practical.

It has been recognized that various cutting devices can be employed at a distal end of a treatment device, and that there is a benefit to being able to track the position of the treatment device when placed within the patient. Such various cutting devices can be incorporated into the above treatment system and thus, can be reciprocated by the reciprocating motor, or the reciprocating action can be omitted and cutting accomplished by the manipulation of the cutting device alone. In one aspect, in order to counter a natural damping that occurs in the superficial space and to facilitate controllable vibration of the cutting structure, the deployable cutting structure is provided with a resonate frequency being a multiplier above vibration delivered in the handle or base associated with the cutting structure.

Figure 7A:
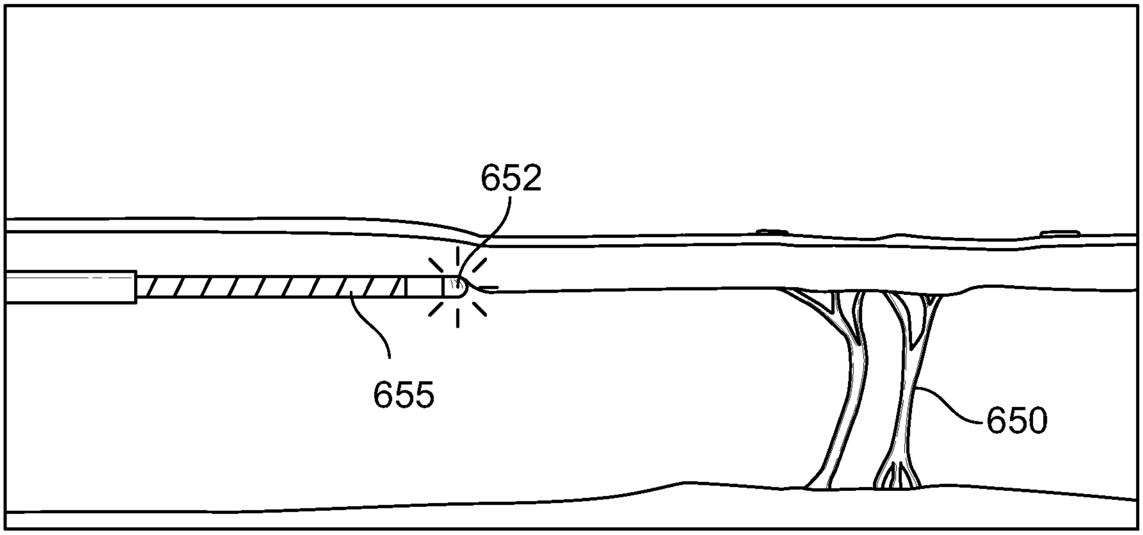
FIGS. 7A-H are partial cross-sectional views, depicting approaches to treating septa below a skin surface.

In another aspect, a distal end portion of a cellulite treatment assembly is inserted through the skin and the tip is guided up into close proximity of the dermis as the tip can be tracked as it is advanced toward septa 650 (FIG. 7A). Given the elasticity of septa 650, the distance from the targeted treatment location to where the treatment assembly is inserted into the skin is preferably at least about 2 cm so that there is enough distance to pull and disrupt septa 650 and not have the tip of the cellulite treatment assembly exit the skin in the process. Additionally, a depth below the skin where septa 650 is preferably engaged (i.e., cut, sliced, torn, stretched, re-oriented (e.g. criss-crossing) or disrupted) is identified and determined. After determining the subcutaneous depth to be accessed for the cutting, slicing, tearing, stretching, re-orienting (e.g. criss-crossing) or disrupting of septum 650, the cellulite treatment assembly or other tool with a sharpened or blunt tip is inserted through the skin, advanced between subcutaneous tissue layers and toward septa 650. In one approach, a distal end portion of the cellulite treatment assembly is configured with an illuminated tip 652 with enough brightness to be seen through the skin. The intensity of light emitted by the tip 652 can be set to a specific constant level such that at the preferred depth below the skin for severing or otherwise engaging septa 650, the light that appears at the level of the skin as a circle or projection is of a pre-determined size. Thus, the treatment device is advanced to the target site. At the target site, the user adjusts the depth of the tip of the treatment tool such that the circle or projection of light is the pre-determined size. The septa 650 is tested and if confirmed as a target for treatment, the septa 650 is treated while maintaining the circle or projection at the pre-determined size. Notably, the diffusion and brightness of light can vary for each patient as the same can be affected by skin tone and body mass index. Thus, calibration can be conducted on a patient by patient basis based upon such factors at the beginning or prior to a procedure. The user can also use the size of the circle or projection of light to maintain the depth of the tip of the treatment tool as it is advanced under the skin to the treatment target. It is expected that the depth that these tools are advanced will be between about 3 and about 10 mm below the skin surface, but it is anticipated that lesser and greater depths may also be optimal for a particular subject. In any event, the depth selected is chosen for cutting, slicing, disrupting, tearing, stretching or re-orienting of the subject's septa 650. Moreover, in one embodiment, it is to be appreciated that the device is formed from a substantially rigid material so that a consistent plane below the skin surface is accessed.

Figure 7B:
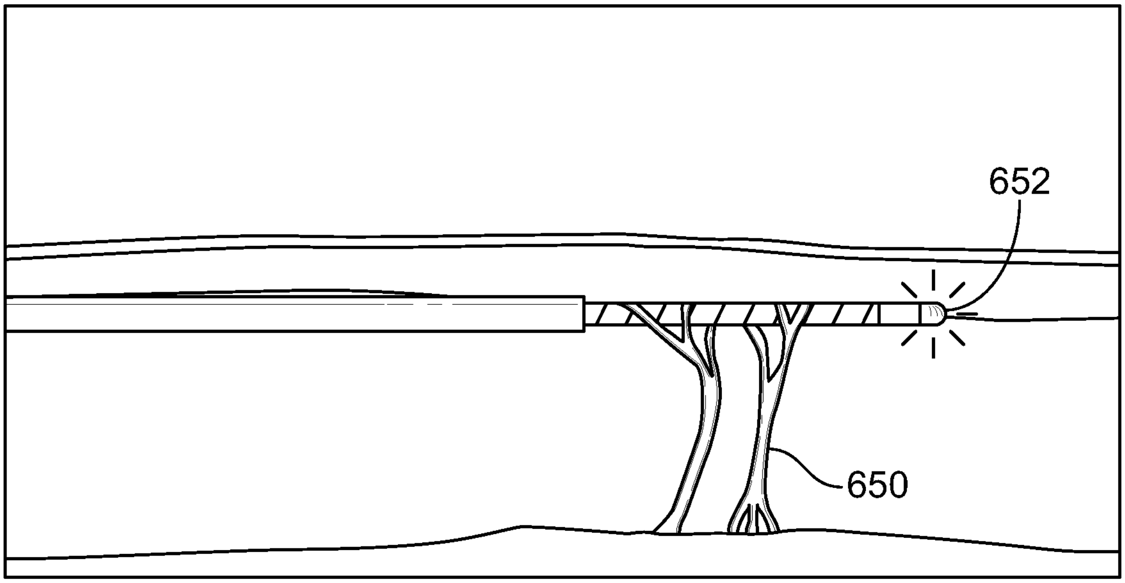
Figure 7C:
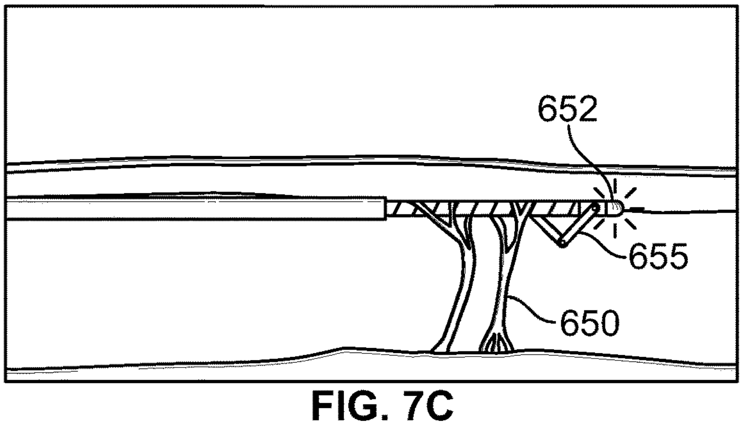
Figure 7D:
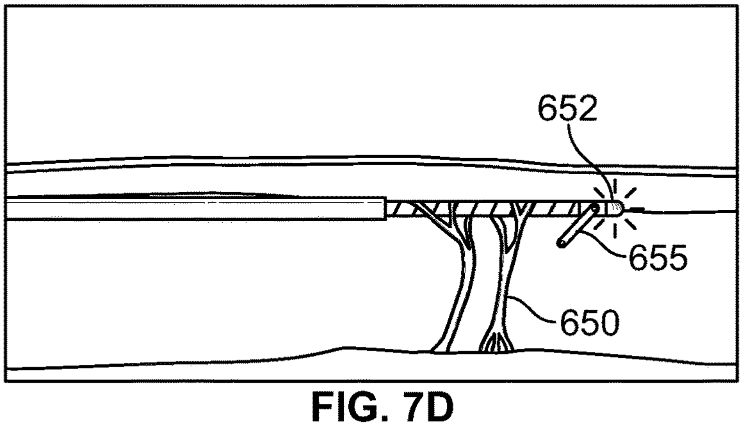
Figure 7E:
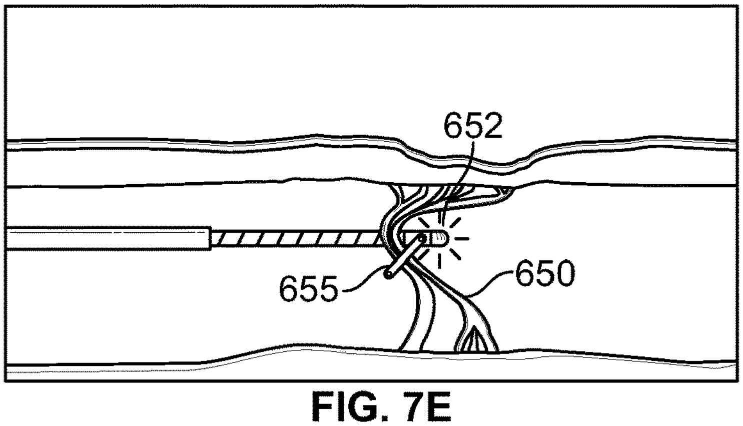

Using palpation, direct visualization (for example, transillumination or endoscopic) or non-invasive visualization (for example, ultrasound or fluoroscopic) or other means for determining the position of the interventional tool such as markings along the length of the instruments and its path within tissue, or providing the interventional instrumentation with radiopaque markers, the tool is placed at a site below where cellulite (for example a dimple) is seen on the subject's skin. The treatment device 655 is advanced through septa 650 and to where the treatment device is in a position best suited to accomplish the identification of target septa and the cellulite removal or minimization treatment. As shown in FIGS. 7B-D, in one approach, the treatment device 655 is passed beyond septa 650, a hook is deployed and then pulled proximally to tension septa 650, such as by hooking the septa (FIG. 7E). In particular, first hooking than cutting septa is advantageous when treating cellulite. In another approach, the treatment device is passed a few millimeters lateral, preferably about 1 to about 10 millimeters, more preferably about 3 to about 6 millimeters, and beyond the target location, a hook is deployed and then moved toward the target followed by pulling proximally to hook and tension septa. During these and other steps, transillumination can be employed to track the treatment device and guide the procedure. The targeting of septa 650 is accomplished while using transillumination to see the location of the treatment device 655. In other approaches, a separate device can be employed to engage septa 650 to see if such septa are the source of a dimple or depression expressed on the outside of the skin. Such a secondary device can be placed remotely from the target (i.e. cellulite depression) and configured to be capable of applying tension to the surface of skin in a predetermined direction so as to create the effect of gravity and produce the visualization of the depressions while the patient is in a prone position (e.g. a broad region of adhesive attached to a spring mechanism such that a predetermined force would be applied relatively parallel to the surface of the skin in the direction the skin would move when standing in gravity). Using this additional device could further help the confirmation and location of depressions and allow confirmation that the treatment was effective. Also, in various approaches, a portion of the elongate member can be configured to transition from a smaller state to a wider or larger state, wherein in the wider or larger state a cutting surface (i.e. sharpened edge or energy) is presented to cut tissue, the device being sized and shaped to be inserted through the skin and engage one or more regions of septa subcutaneously.

Figure 7F:
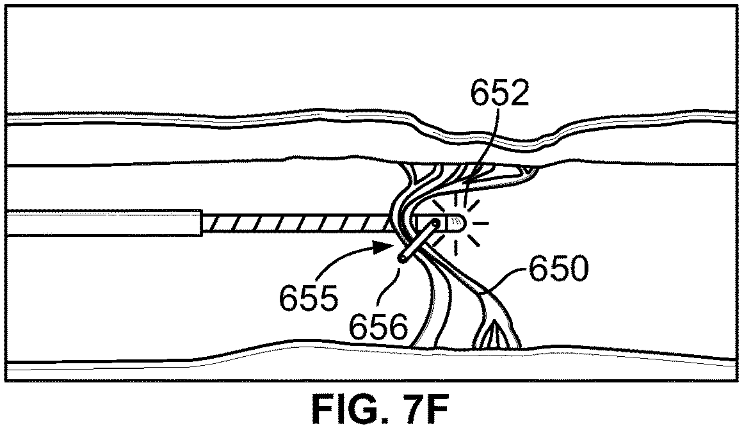

It is noted that septa causing a dimple or depression may be coming from various angles and locations relative to the dimple or depression seen on the skin rather than being directly below the dimple or depression, and may be due to one or only a few septa or a large number of septa that remotely cause the depression or dimple. Thus, so engaging certain septa will be reflected in some change in the dimple or depression on the skin. A determination is made concerning the correspondence with targets on the skin and the dimples being formed or re-formed. If the initial septa 650 that the user presses on or pulls on using the tool do not recreate a dimple or depression in the targeted area, then the user releases those initial septa that were engaged and repositions the tool at different septa and presses on or pulls again. This is repeated until the septa responsible for a dimple or depression in the marked location are identified. Once proper septa are identified, the tool is manipulated to cut, slice, disrupt, re-orient, stretch or tear septum 650 connecting tissue layers. In one approach, a blade 656 is deployed and presented for treatment (FIG. 7F).

Figure 7G:
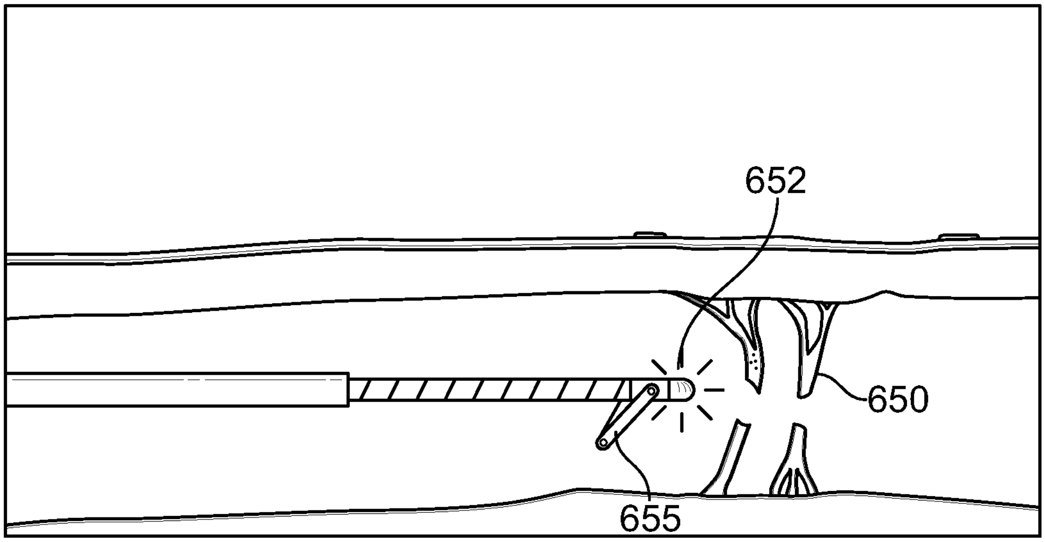
Figure 7H:
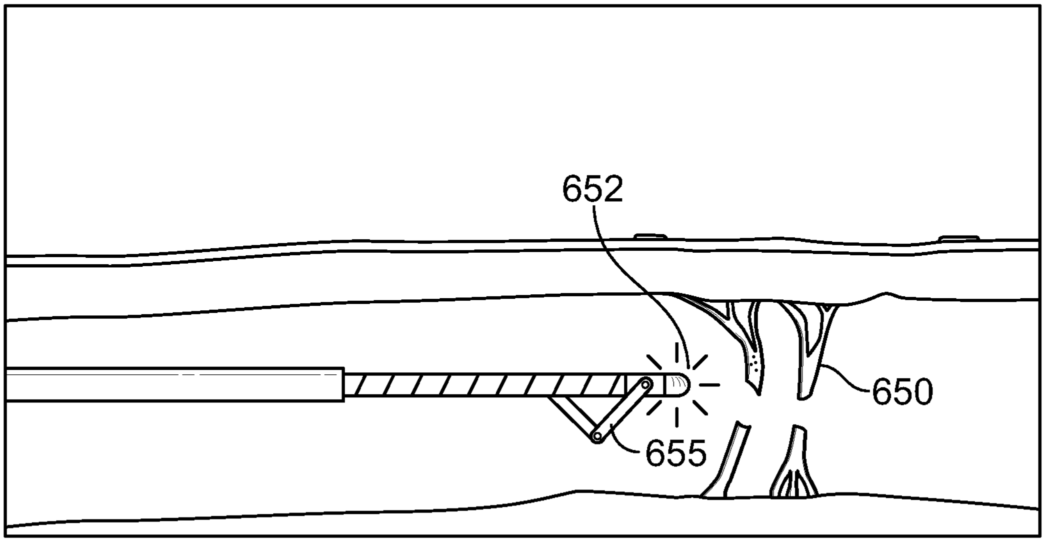

After the proper septa have been cut, sliced, disrupted, stretched, re-oriented or torn, the treatment element is moved back to its initial collapsed configuration. The treatment element is then advanced beyond the marked treatment location, the treatment element (e.g., hooking and cutting device) is deployed and then pulled back under the marked treatment location to confirm that all of the septa responsible for causing the marked dimple or depression have been separated intra-operatively. If they have not been, the tool is manipulated to cut, slice, disrupt, stretch, re-orient or tear additional septa. The steps are repeated until all of the septa responsible for creating the marked dimple or depression have been severed or sufficiently stretched and the dimple or depression cannot be re-created intra-operatively using the tool. Such manipulation results in selective rupture, tearing, cutting or slicing of targeted septum 650, and the removal or minimization of dimples and the expression of cellulite on skin (FIG. 7G). Thereafter, the treatment element (e.g., hook and/or blade) is retracted back in (FIG. 7H partially collapsed) and the tool is removed from the site to be withdrawn from the body or repositioned in any direction along and within the target tissue plane to treat additional areas.

Figure 8A:
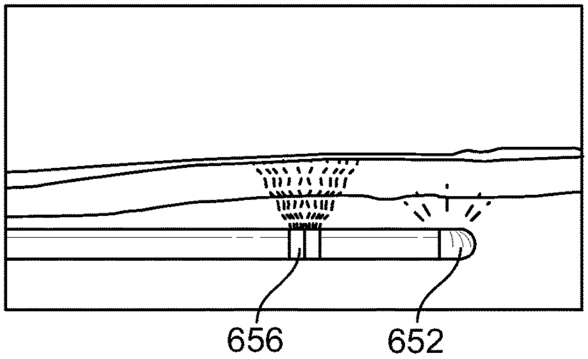
FIGS. 8A-D are side and top views partially in cross-section, depicting an alternative approach to transillumination.
Figure 8B:
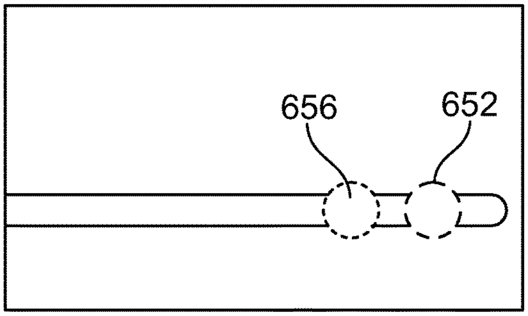
Figure 8C:
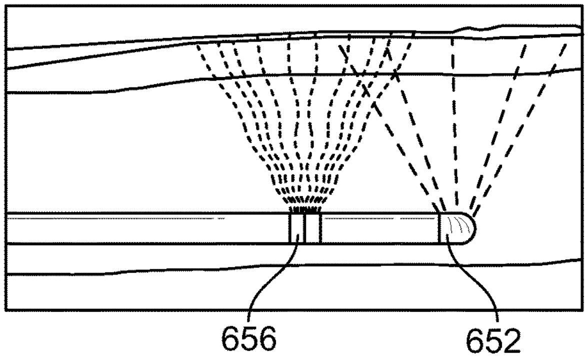
Figure 8D:
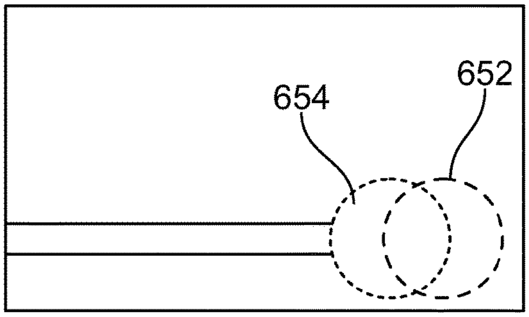

With reference to FIGS. 8A-D, in additional or alternative approaches, a second light source 656 such as an LED (or other light source) is configured along the cellulite treatment assembly proximal the illuminated tip 652 or alternatively, at the tip 652. In various approaches, a light source such as an LED chip can be configured at the tip of or otherwise along the treatment device with an electrical wire running proximally for control by the operator, or the light source can be generated by a light fiber extending along the device or to the tip with the LED or light source is configured within a proximally located position such as a handle of the treatment device. By so configuring such light sources 652, 656, the depth of the cellulite treatment assembly within tissue can be assessed. As shown in FIGS. 8A-B, when the cellulite treatment assembly is placed within a first relatively shallow desired depth, the light sources 652, 656 appear spaced and define discrete patterns when viewing the light sources via transillumination through skin (FIG. 8B). When the cellulite treatment assembly is placed deeper within tissue (FIGS. 8C-D), the light sources 652, 656 overlap (FIG. 8D) due to the natural dispersion of light emitted from the light sources 652, 656. An operator of the treatment system can determine a depth of the cellulite treatment assembly by noting the discrete patterns of light or the degree of overlap of light overlap, the dispersion of light emitted and intensity of the light emitted from the light sources 652, 656. Thus, allowing the operator to guide the distal end of the treatment assembly to the desired treatment location while maintaining the desired depth below the skin. The light sources 652, 656 can also be of a different color to aid in determining the orientation of the cellulite treatment system within tissue through illumination. Moreover, the second light source 656 can emit a red color, for example, while the illuminated tip 652 can emit white light, while noting any variation of colors can also be employed. Also, the color of the light can change depending on the configuration of the treatment device, such as for example, the device can project a white or first color when sheathed or stowed and change to another color or second color when a portion of the device is deployed or before and after use such as when tissue is cut. A strain gauge can be configured to communicate and cooperate with the light source to sense loads placed on the treatment device during treatment to thereby facilitate a change in color of the light source and to signal the progress or completion of targeted treatment. Additionally, the second light source 656 can be employed via transillumination through skin to locate the cellulite treatment system relative to a treatment target area. Another benefit of the second light source is that it can indicate to the user where the hook and blade are located relative to the target septa. Also, as the treatment tool is being pulled proximally through the treatment target area, the illuminated tip 652 lets the user know when the hook and blade have been pulled through the target area. It is further noted that the light sources 652, 656 can be positioned at various alternative locations along a treatment device, and can be spaced from each other by various amounts. Also, the cellulite treatment system can include greater than two light sources of the same or dissimilar colors. In another embodiment, different colors of light can be used to indicate that the state of the distal end of the instrument. For example, red light is used to indicate the hook and blade are inside the instrument for advancing under the skin, white light is then used to indicate the hook is deployed, and red light is then used to indicate when the blade is deployed.

Figure 9:
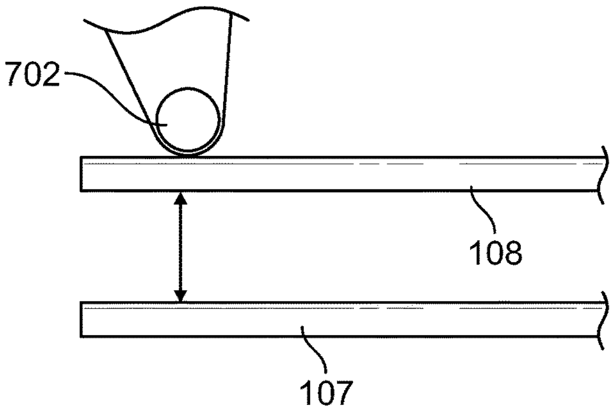
FIG. 9 is a cross-sectional view, depicting a sensor apparatus for determining positional and depth information of a treatment device.

In another approach, as shown in FIG. 9, a sensor apparatus 702 that communicates with structure or a sensor on the treatment device 107 is employed to determine the position and depth of the treatment device 107 below the skin 108. The sensor apparatus 702 can employ a magnetic field, metal detection or ultrasound to accomplish gathering such positional and depth information on the treatment device 107. This information can further be communicated directly to the operator via a display or through a controller associated with the treatment device.

After completing treatment of one target area, the procedure is repeated to treat other target areas. Accordingly, the same device can be employed to access tissue layers below other sites or depressions existing in skin. Notably, in one embodiment, the device is capable of anesthetic delivery as needed or desired when progressing to additional or new locations. There is thus provided a system configured to treat all target areas on the buttocks and thigh through a limited number of small entry sites, including through a single entry site on a patient's treated side. It is to be recognized that the system can further include structure permitting the assembly to be steerable to subcutaneous treatment sites. In such an embodiment, the device would be configured to define longitudinally flexible material, and the instrumentation would be steered to the desired position within tissue. Moreover, in certain applications, the device has a stiffness that varies along its length. In another embodiment, the treatment device is embodied in a deflectable catheter.

Additionally, or alternatively, in each disclosed embodiment, illumination can be via a lightguide from an external light source or via one or more LEDs external or internal the treatment device. Illumination aids the user both with locating the treatment device as well as proper depth placement as transillumination decreases with increasing tool depth. In one aspect, the amount of illumination is set to ensure proper depth of a treatment device or structure, the level of illumination targeted being adjusted for skin type, thickness, presence of fat and pigment. Once selected or targeted septa are cut, sliced or disrupted, in each of the disclosed approaches, the cellulite treatment device can be or is advanced or repositioned to treat additional target areas from the same or different skin insertion location.

Various approaches to laterally projectable tissue engaging and/or cutting structure can be employed. Here again, so engaging septa can confirm that the septa responsible for creating skin surface dimples or depressions is being targeted as such engagement with septa will be reflected in a physical change of the skin surface. Transillumination functionality is provided by a light at a terminal end of the device, or formed in the shaft proximal the terminal end allows for the dispersion of light energy. Actuation of the engaging and cutting structures can be accomplished through the manipulation of a proximally positioned lever or trigger connected to the same via a wire or longitudinally directed shaft (not shown). Once a desired area is treated, additional target areas can be addressed.

Figure 10A:
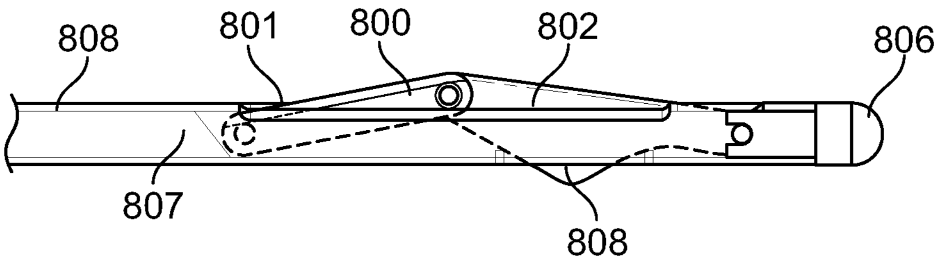
FIGS. 10A-C are top views, depicting further approaches to cutters for a treatment system.
Figure 10B:
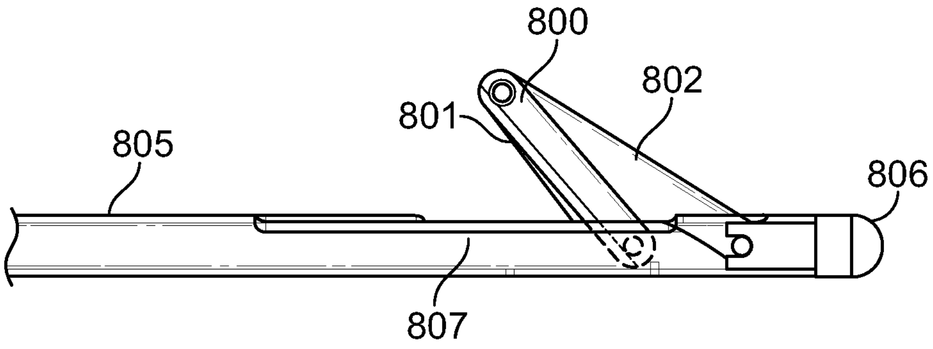
Figure 10C:
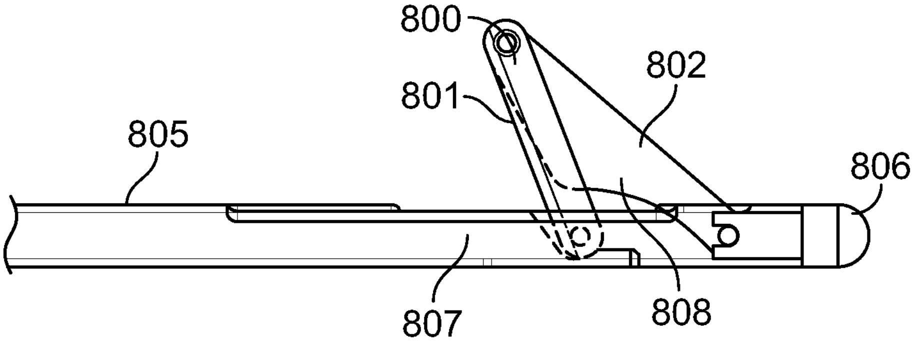

With reference to FIGS. 10A-C, the cutting, slicing or disrupting treatment assembly is defined by a projecting linkage arrangement. A first link 800 includes a blade 801 and is rotatably attached at one end to a second link 802. The opposite end of the first link 800 slides with respect to a longitudinal shaft 805 (shown as at least partially transparent). The shaft 805 defines a housing for supporting and containing the linkage arrangement. A second end of the second link 802 is rotationally affixed to a distal point on the shaft 805. A drive shaft or push rod 807 is rotatably or pivotably attached to the opposite end of the first link 800 and the second link 802 includes a generally triangular or pointed projection 808 that is sized and shaped to shield the blade 801 from contacting tissue when the assembly is placed in a hooking configuration. When the push rod 807 is fully retracted (FIG. 10A), the blade 801 is sheathed within the body of the longitudinal shaft 805. It is noted that in the fully retracted configuration that the first and second links 800, 801 form an obtuse angle and the projection 808 extends a relatively small distance from an opposite side of the longitudinal shaft. When the push rod 807 is advanced completely to a stop, the projection 808 contacts the push rod 807 and the blade 801 is again protected by the projection 808 (FIG. 10B). It is in this configuration that the treatment device can be used to hook target septa and to test septa to determine if such septa is associated with the expression of cellulite on a patient's skin. Withdrawing the push rod 807 from its fully advanced position and to a partially withdrawn position (See FIG. 10C where the blade 801 is shown transparent for illustrative purposes), the blade 801 is exposed and presented for engaging and cutting, slicing or disrupting target septa. The treatment device also has a blunt, atraumatic tip 806 (such as a conical profile for example) that allows the treatment device to be advanced through the subcutaneous tissue with little trauma. In all embodiments, blunt tip 806 can house a light emitting diode, be a light emitting diode or house the end of a light fiber in order to facilitate transillumination through the skin for the user to use for guidance in knowing the location of the tip of the treatment device.

It is to be recognized that additionally or alternatively, the tip in any of the disclosed embodiments can be shaped so as to be characterized by or associated with a low introduction and advancement force through and within the patient's skin and anatomy, while also presenting a low likelihood of damaging tissue. Accordingly, the tip can assume bullet point or short dilator tip shapes, or can define a sharp profile or a trocar-type configuration for ease of advancement or tracking. Additionally, the tip can be retractable, reconfigurable or otherwise define a sharpened structure only when the tip is presented with a pre-determined level of resistance. In one particular approach, a spring loaded cover or shield is configured about the tip such that when presented with a defined resistance, the cover or shield is removed to expose a sharpened tip configured to facilitate advancement of the treatment device or reduce the force to cross patient anatomy.

Figure 11A:
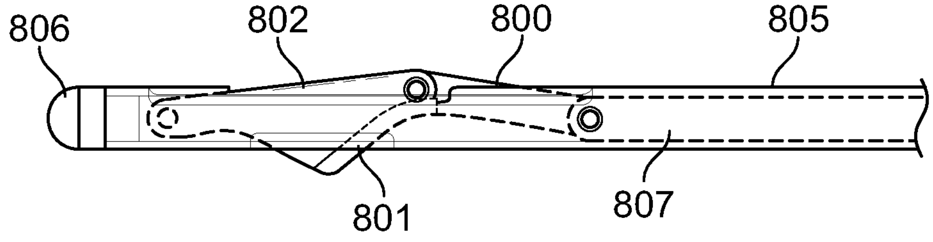
FIGS. 11A-F are bottom and top views, depicting yet other further approaches to cutters for a treatment system.
Figure 11B:
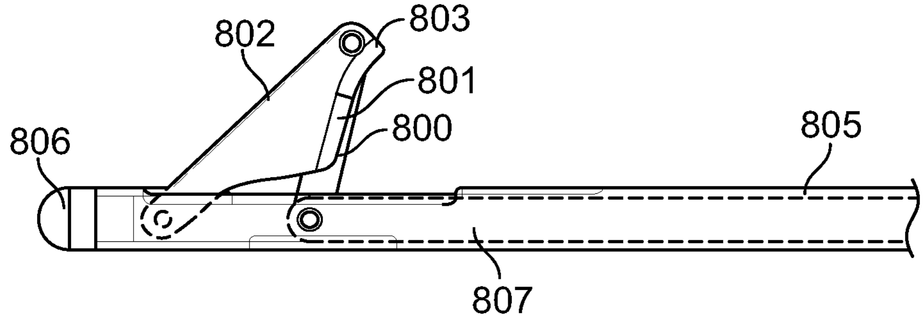
Figure 11C:
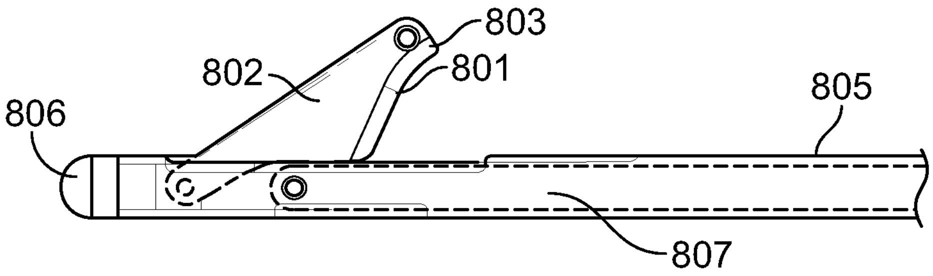
Figure 11D:
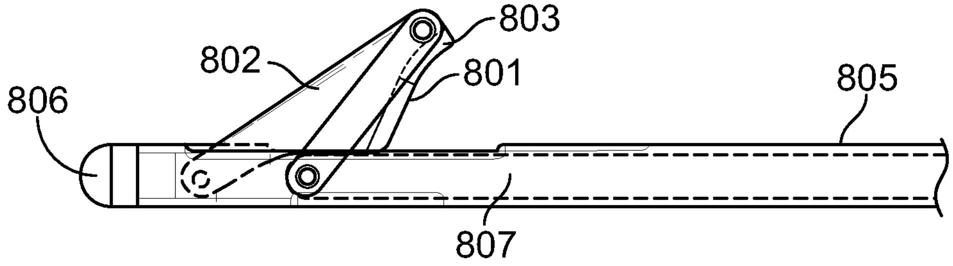

In one or more approaches, the second link 802 includes a blade 801 that has a sharpened protrusion 803, and the first link 800 functions as a blocker to shield a main portion of the blade 801 from contacting tissue when the treatment device is in the hooking configuration (See FIGS. 11A-F). When the treatment device is in the hooked configuration, the sharpened protrusion 803 extends proximally from the pivot between the first link 800 and second link 802 so that as the treatment device is pulled proximally by the user, the pivot location, as the leading portion of the device during retraction, does not get snagged in tissue but rather slices through it so the user can hook and feel resistance of septa with the main portion of the first link 800. Notably, in a fully retracted position (FIG. 11A), the first and second links 800, 801 define an obtuse angle and when the push rod 807 is advanced nearly completely (FIG. 11B), a majority of the blade 801 is protected by the second link 802. As such, structure is presented in a hook-form both to encourage hook capture as well as provide a portion of unprotected blade 803 near the connection between the first and second 800, 802 links. Completely advancing the push rod 807 fully exposes the blade 801 for cutting, slicing or disrupting target septa (See FIGS. 11C-D; FIG. 11D showing the first blade as transparent for illustrative purposes) as the treatment device is retracted proximally by the user.

Figure 11E:
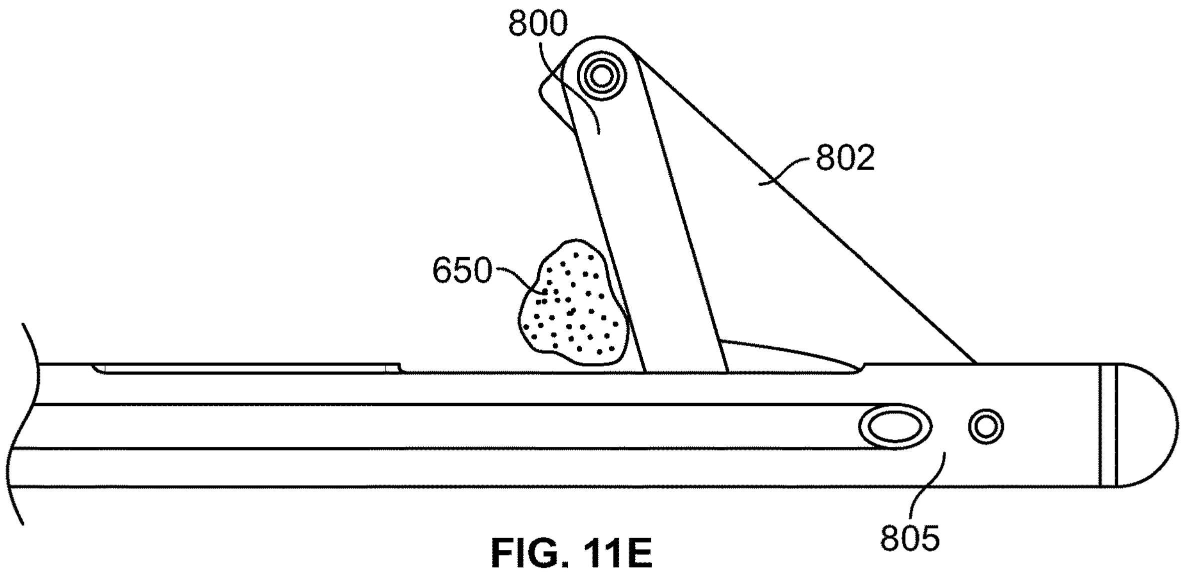
Figure 11F:
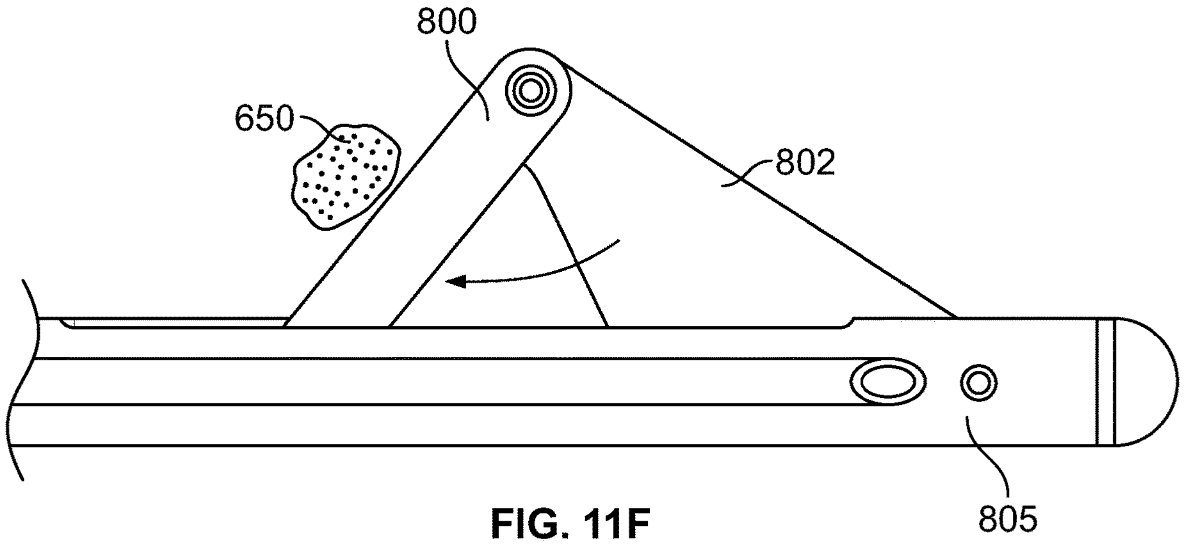

In employing one or more of the disclosed embodiments in a treatment procedure, there is an expectation that there are instances where it is preferable to not disrupt a hooked septa, and in such a case it is desirable to release or disengage the hooked septa. In certain approaches, to release or disengage, the treatment device would be advanced or twisted away from the hooked septa. It is thus recognized that a challenge exists in that there may be additional septa or other tissue in the area which could be unintentionally re-engaged by the treatment device when it is in a hooking configuration, and stowing of the treatment device may be inhibited by adjacent patient anatomy. With reference to FIGS. 11E-F, treatment devices that include a hinge link arrangement 800, 802 or similar structure that transition from a hooked configuration (FIG. 11E) toward a stowed configuration (FIG. 11F) by pivoting relative to the longitudinal shaft 805, benefit from the blocking link 800 (or similar structure) moving to push septa 650 or other tissue away from the treatment device as the treatment device is being sheathed or stowed. This action requires no additional advancement of the treatment device within patient anatomy and ensures that septa 650 or other tissue do not become undesirably entrapped. Moreover, when being stowed the links 800, 802 dislodge any tissue that might have become captured within the longitudinal shaft 805 and the links 800, 802 ultimately occupy such spaces within the longitudinal shaft 805.

The treatment tool embodiments of FIGS. 7A to 11F can be used in previously described hand piece embodiments. The illuminated tip can be used in the previously described cutting tools 102.

Figure 12A:
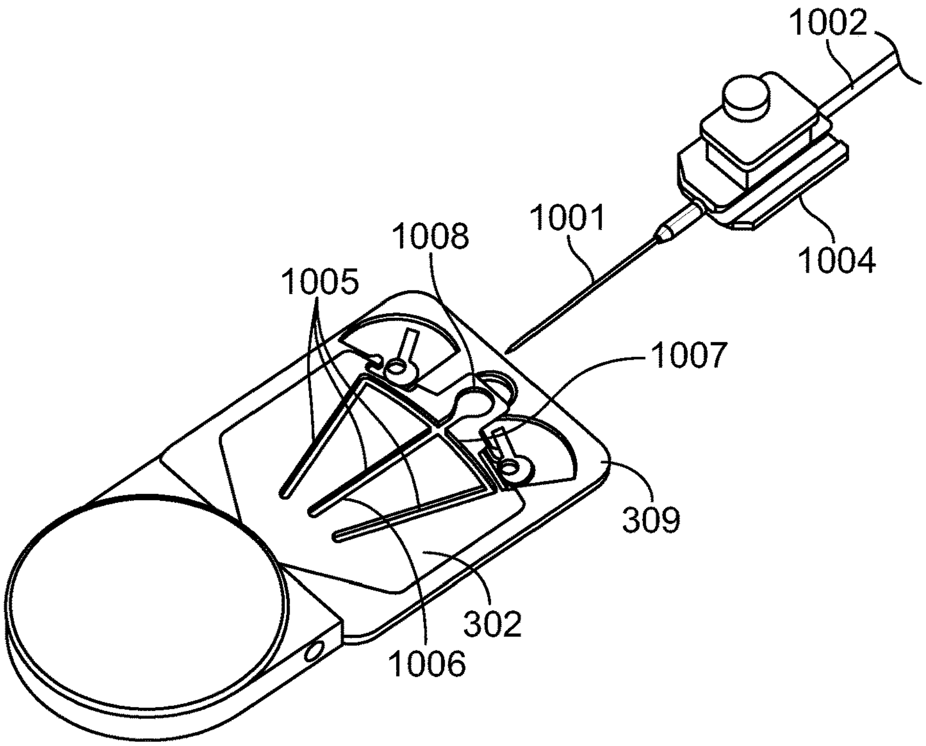
FIGS. 12A-C are perspective views, depicting a fluid delivery system.
Figure 12B:
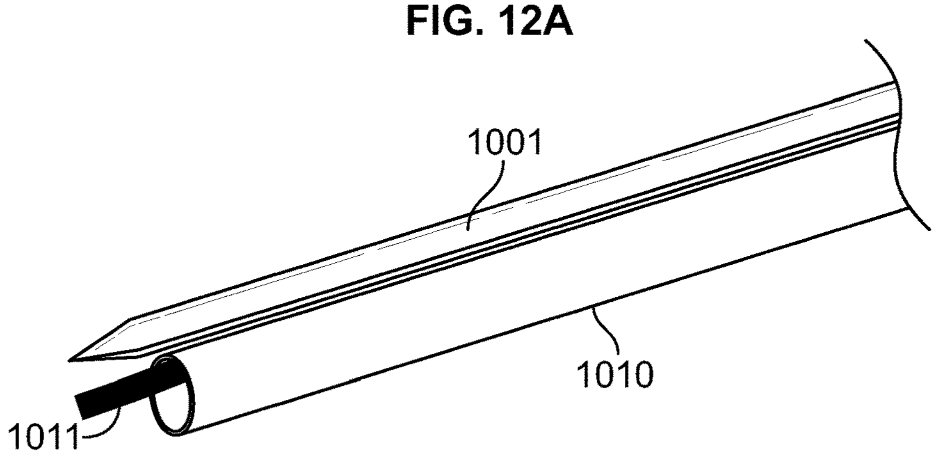
Figure 12C:
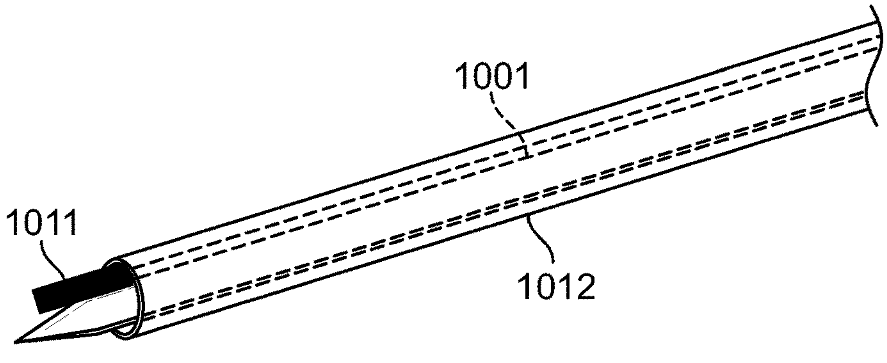

Turning to FIGS. 12A-C, guidance track 302 is configured to provide a controlled delivery of treatment fluid through needle 1001. Needle 1001 may be a tube, an hypodermic needle and may have a multitude of holes for increased lateral fluid dispersion. A supply tube 1002 provides fluid connection of needle 1001 with a syringe 1003, syringe pump, roller pump or other injection mechanism known in the art. In certain embodiments, a needle control module 1004 is included to house needle 1001 and to provide support for movement along guidance track 302. It is to be recognized however that one or more of the alternative or additional components and structures disclosed herein can replace the guidance track, and various handpieces can be combined with the needle assembly. As shown, movement of needle 1001 along guidance track 302 provides delivery of the treatment fluid in precise locations of the dissection region and minimizes the amount of infusion fluid required for a single treatment and/or over multiple treatment sites. Needle control module 1004 preferably includes a guide pin to be engaged into guidance track 302 of platform 309. The guide pin guides the needle/cannula to insure that the injectable fluid is injected into the tissue at the desire depth and desired locations within a predefined treatment area defined by the path of guidance track 302.

As best seen in FIGS. 12B-C, in an alternative embodiment, structure is provided for receiving a light source such as a light fiber or an LED. In one approach (FIG. 12B), extending along the needle 1001 is a lumen 1010 sized and shaped to receive a light source 1011. In another approach (FIG. 12C), a sleeve 1012 is configured about the needle 1001 and the sleeve includes a inner lumen or space for receiving the light source 1011. In this way, the position of the needle 1001 can be tracked and/or anatomy can be viewed during an interventional treatment procedure.

Accordingly, various approaches to cellulite treatment methods and apparatus are presented. The disclosed approaches are configured to provide an effective and focused approach to treating, minimizing and preventing cellulite. The disclosed approaches can also be used to repair and reduce the appearance of cellulite in a targeted manner. Further, the disclosed proactive treatment modalities are easy and effective to use.

Some of the specific aspects of the present disclosure include one or more of focal treatment of just the septa responsible for causing dimples or depressions in the skin; minimizing bruising; accessing all treatment targets from limited, cosmetically acceptable entries; capture and retention of septa while separating the septa; intra-operative confirmation of treated target; needle-diameter sized tools for small openings; and transillumination identification of tool tip location.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A system for treating an expression of cellulite on skin of a patient, the system comprising:

a handpiece including:

a base having a chamber and a conduit, wherein the conduit provides access to the chamber, an upper portion having an upper platform and a lower platform, wherein the upper portion is above the chamber, and the lower platform has an adhesive on a lower surface configured to engage the skin, and a spring positioned between the base and the upper platform and around the lower platform, wherein the spring is configured to bias the upper portion upwardly to lift the skin; and a treatment device having a shaft and a septa engaging assembly attached to the shaft, wherein the shaft is configured to be inserted through the conduit and through the skin received in the chamber, and the septa engaging assembly is configured to engage a septum to treat the expression of cellulite.

2. The system of claim 1, wherein the treatment device has a light configured to generate transillumination.

3. The system of claim 2, wherein the light is positioned along a distal portion of the shaft.

4. The system of claim 2, wherein the light is one or more of an LED and/or a lightguide.

5. The system of claim 1, wherein the treatment device is steerable.

6. The system of claim 1, wherein the septa engaging assembly includes a side opening hook.

7. The system of claim 1, further comprising a source of suction for pulling the skin in the chamber.

8. The system of claim 1, wherein the treatment device includes a first link and a second link, the first link includes a blade, and the second link is configured to shield the blade from contacting tissue when the treatment device is in a hooking configuration.

9. The system of claim 8, wherein the first link has a first end pivotably attached to the shaft.

10. The system of claim 1, wherein the upper platform has a width larger than a width of the lower platform.

11. The system of claim 1, wherein the base is ring-shaped.

12. The system of claim 1, wherein the base has an upper opening configured to receive the upper portion.

13. The system of claim 1, wherein the handpiece has a second conduit, wherein the shaft is configured to be inserted through the second conduit.

14. The system of claim 13, wherein the conduit and the second conduit are circumferentially disposed around a perimeter of the base.

15. The system of claim 1, wherein the treatment device has an actuator configured to actuate the septa engaging assembly between a concealed configuration, a septa tensioning configuration, and a septa disruption configuration.

* * * * *